United States Patent
Hameed Peer Mohamed et al.

(10) Patent No.: US 9,957,253 B2
(45) Date of Patent: May 1, 2018

(54) TRIAMINOPYRIMIDINE COMPOUNDS USEFUL FOR PREVENTING OR TREATING MALARIA

(71) Applicant: MMV MEDICINES FOR MALARIA VENTURE, Geneva (CH)

(72) Inventors: Shahul Hameed Peer Mohamed, Bangalore (IN); Vikas Patil, Bangalore (IN); Kannan Murugan, Tirunelveli (IN); Eknath Vithalrao Bellale, Latur (IN); Anandkumar Raichurkar, Bangalore (IN); Sudhir Landge, Bangalore (IN); Jayashree Puttur, Bangalore (IN); Nilanjana Roy Choudhury, Bangalore (IN); Gajanan Shanbhag, Bangalore (IN); Krishna Koushik, Bangalore (IN); Pravin Iyer, Bangalore (IN); Vasan Kirthika Sambandamurthy, Bangalore (IN); Suresh Solapure, Bangalore (IN); Shridhar Narayanan, Bangalore (IN)

(73) Assignee: MMV MEDICINES FOR MALARIA VENTURE, Geneva (CH)

( * ) Notice: Subject to any disclaimer, the term of this patent is extended or adjusted under 35 U.S.C. 154(b) by 0 days. days.

(21) Appl. No.: 15/307,382

(22) PCT Filed: Mar. 26, 2015

(86) PCT No.: PCT/EP2015/056496
§ 371 (c)(1),
(2) Date: Oct. 28, 2016

(87) PCT Pub. No.: WO2015/165660
PCT Pub. Date: Nov. 5, 2015

(65) Prior Publication Data
US 2017/0050951 A1    Feb. 23, 2017

(30) Foreign Application Priority Data
Apr. 28, 2014  (IN) .......................... 2142/CHE/2014

(51) Int. Cl.
*C07D 401/14* (2006.01)
*C07D 403/14* (2006.01)
*A61K 31/506* (2006.01)
*A61K 45/06* (2006.01)

(52) U.S. Cl.
CPC .......... *C07D 401/14* (2013.01); *A61K 31/506* (2013.01); *A61K 45/06* (2013.01); *C07D 403/14* (2013.01)

(58) Field of Classification Search
CPC ..... A61K 45/06; A61K 31/506; C07D 401/14
See application file for complete search history.

(56) References Cited

U.S. PATENT DOCUMENTS

2009/0048250 A1    2/2009 Aronov et al.

OTHER PUBLICATIONS

Deng, X. et al. "Discovery of novel 1H-imidazol-2-yl-pyrmidine-4,6-diamines as potential antimalarials" *Bioorganic & Medicinal Chemistry Letters*, 2010, pp. 4027-4031, vol. 20.
Fidock, D. A. et al. "Antimalarial Drug Discovery: Efficacy Models for Compound Screening" *Nature Reviews*, Jun. 2004, pp. 509-520, vol. 3.
Hameed, S. P. et al. "Triaminopyrimidine is a fast-killing and long-acting antimalarial clinical candidate" *Nature Communications*, Mar. 31, 2015, pp. 1-11, vol. 6.
Johnson, J. D. et al. "Assessment and Continued Validation of the Malaria SYBR Green I-Based Fluorescence Assay for Use in Malaria Drug Screening"*Antimicrobial Agents and Chemotherapy*, Jun. 2007, pp. 1926-1933, vol. 51, No. 6.
Le Manach, C. et al. "Fast in vitro methods to determine the speed of action and the stage-specificity of anti-malarials in Plasmodium falciparum" *Malaria Journal*, 2013, pp. 1-7, vol. 12, No. 424.
Marfurt, J. et al. "Ex Vivo Drug Susceptibility of Ferroquine against Chloroquine-Resistant Isolates of *Plasmodium falciparum* and *P. vivax*" *Antimicrobial Agents and Chemotherapy*, Sep. 2011, pp. 4461-4464, vol. 55, No. 9.
Trager, W. et al. "Human Malaria Parasites in Continuous Culture" *Science*, Aug. 20, 1976, pp. 673-675, vol. 193, No. 4254.
Written Opinion in International Application No. PCT/EP2015/056496, dated Jun. 3, 2015, pp. 1-6.

*Primary Examiner* — Alexander R Pagano
*Assistant Examiner* — Ebenezer O Sackey
(74) *Attorney, Agent, or Firm* — Saliwanchik, Lloyd & Eisneschenk

(57) ABSTRACT

The present invention relates to triaminopyrimidines and to pharmaceutically acceptable salts thereof, to their use in the treatment and/or prevention of malaria caused by *plasmodium* species, and to their methods of preparation.

23 Claims, No Drawings

TRIAMINOPYRIMIDINE COMPOUNDS USEFUL FOR PREVENTING OR TREATING MALARIA

CROSS-REFERENCE TO RELATED APPLICATION

This application is the U.S. national stage application of International Patent Application No. PCT/EP2015/056496, filed Mar. 26, 2015.

FIELD OF THE INVENTION

The present invention relates to triaminopyrimidine compounds, pharmaceutical compositions thereof, and methods of use. In addition, the present invention relates to therapeutic methods for the treatment of parasitic infections caused by *plasmodium* species.

BACKGROUND OF THE INVENTION

Malaria is caused by protozoan parasites of the genus *Plasmodium* that infect and destroy red blood cells, leading to fever, severe anemia, cerebral malaria and, if untreated, death. *Plasmodium falciparum* is the dominant species in sub-Saharan Africa, and is responsible for approximately 600,000 deaths each year. The disease burden is heaviest in African children under 5 years of age and in pregnant women. *Plasmodium vivax* causes 25-40% of the global malaria burden, particularly in South and Southeast Asia, and Central and South America. The other three main species that are known to infect humans are *Plasmodium ovale, Plasmodium knowlesi* and *Plasmodium malariae*. *Plasmodium* species, for example, *P. falciparam* and *P. vivax* which are known to cause malaria are particularly important because of the development of resistant strains which are both difficult to treat and difficult to eradicate from the hospital and community environment once they have established infection. Examples of such strains are chloroquine resistant, pyrimethamine resistant, artemisinin resistant strains of *Plasmodium falciparum*.

Malaria is a disease that is prevalent in many developing countries. Approximately 40% of the world's population lives in countries where the disease is endemic; approximately 247 million people suffer from the disease every year.

Consequently, in order to overcome the threat of widespread multi-drug resistant parasites, there is an urgent need to develop new antimalarial agents particularly those with either a novel mechanism of action and/or containing new pharmacophoric groups.

The present invention aims at addressing such drawbacks in the art associated with the management and treatment of malaria.

SUMMARY OF THE INVENTION

In accordance with the present invention, the applicants have hereby discovered compounds that possess the ability to act as antimalarial agents.

The present invention provides compounds of Formula (I):

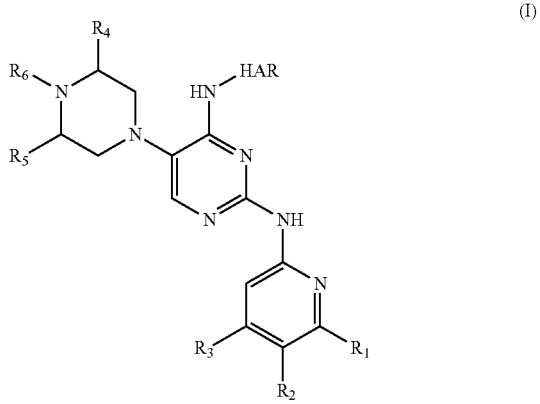

and pharmaceutically acceptable salts thereof, wherein HAR, $R^1$, $R^2$, $R^3$, $R^4$, $R^5$ and $R^6$ are defined below.

The present invention also provides processes for the preparation of compounds of Formula (I), pharmaceutical compositions containing them as the active ingredient, their use as medicaments, methods of using such compounds, and their use in the manufacture of medicaments for the prevention and treatment of malaria in warm blooded animals such as human beings.

It is expected that typical compounds of Formula (I) possess beneficial and efficacious metabolic, toxicological, and/or pharmacodynamic properties.

DETAILED DESCRIPTION OF THE INVENTION

The present invention provides compounds of Formula (I):

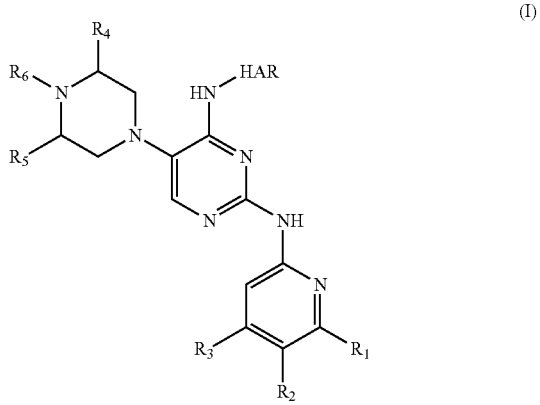

as well as complexes, hydrates, solvates, or polymorphs, tautomers, geometrical isomers, optically active forms and pharmaceutically acceptable salts thereof, wherein:

HAR is a 5 membered heteroaryl ring system selected from the following group:

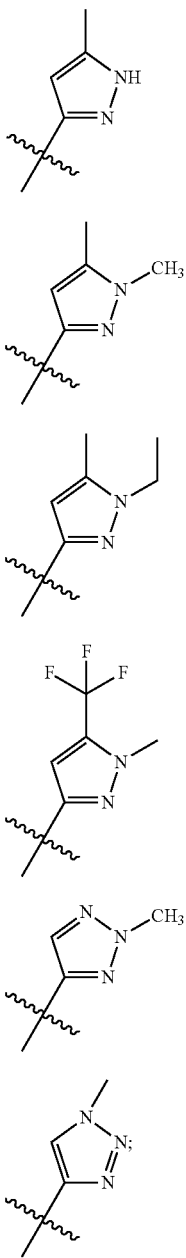

(a)
(b)
(c)
(d)
(e)
(f)

$R^1$ in each occurrence is independently selected from H, $C_{1-6}$ alkyl, $CF_3$ and $C_3-C_5$ cycloalkyl;

$R^2$ in each occurrence is independently selected from halo, —CN and $C_{1-6}$ alkyl;

$R^3$ each occurrence is selected from H, $C_{1-6}$ alkyl, $C_3-C_5$ cycloalkyl and $CF_3$;

$R^4$ in each occurrence is independently selected from H and $C_{1-6}$ alkyl;

$R^5$ in each occurrence is independently selected from H and $C_{1-6}$ alkyl; and $R^6$ in each occurrence is independently selected from H and $C_{1-6}$ alkyl.

In some embodiments, $R^1$ is methyl.

According to another embodiment, $R^2$ is halogen.

In some embodiments, $R^2$ is selected from fluorine, chlorine and CN.

According to a further embodiment, $R^2$ is F or Cl.

According to another embodiment, $R^3$ is $C_3-C_5$ cycloalkyl such as cyclobutyl or cyclopropyl.

According to another embodiment, $R^3$ is cyclopropyl.

According to another embodiment, $R^3$ is $C_{1-6}$ alkyl such as ethyl.

In some embodiments, $R^3$ is selected from cyclobutyl, ethyl and cyclopropyl.

According to another embodiment, $R^4$ is H.

According to another embodiment, $R^4$ is $C_{1-6}$ alkyl such as methyl.

In some embodiments, $R^4$ is selected from hydrogen and methyl.

In some embodiments, $R^5$ is hydrogen.

According to another embodiment, $R^6$ is H.

According to another embodiment, $R^6$ is $C_{1-6}$ alkyl such as methyl.

In some embodiments, $R^6$ is selected from hydrogen and methyl.

In some embodiments, HAR is selected from the following group:

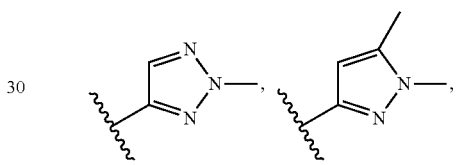

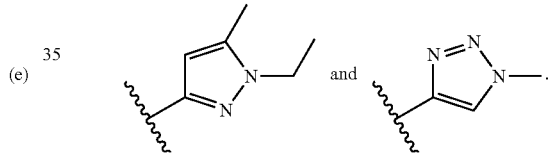

According to another embodiment, HAR is selected from

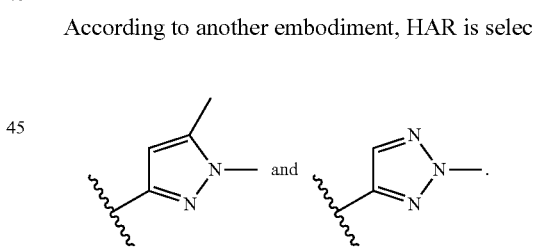

According to another particular embodiment, is provided a compound of Formula (I) wherein wherein $R^1$ is methyl; $R^2$ is selected from fluorine, chlorine and CN; $R^3$ is selected from cyclobutyl, ethyl and cyclopropyl; $R^4$ is selected from hydrogen and methyl; $R^5$ is hydrogen; $R^6$ is selected from hydrogen and methyl; and HAR is selected from the following group:

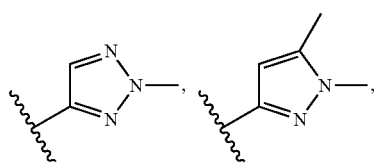

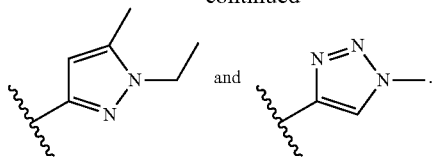

In this specification the prefix $C_{x-y}$ as used in terms such as $C_{x-y}$ alkyl and the like (where x and y are integers) indicates the numerical range of carbon atoms that are present in the group; for example, $C_{1-6}$ alkyl includes $C_1$alkyl (methyl), $C_1$alkyl (ethyl), $C_3$ alkyl (propyl and isopropyl) and $C_4$ alkyl (butyl, 1-methylpropyl, 2-methylpropyl, and t-butyl).

Unless specifically stated, the bonding atom of a group may be any suitable atom of that group; for example, propyl includes prop-1-yl and prop-2-yl.

Alkyl—As used herein the term "alkyl" refers to both straight and branched chain saturated hydrocarbon radicals having the specified number of carbon atoms. References to individual alkyl groups such as "propyl" are specific for the straight chain version only and references to individual branched chain alkyl groups such as 'isopropyl' are specific for the branched chain version only. In one aspect, "$C_{1-6}$alkyl" may be methyl.

Cycloalkyl—As used herein, the term "cycloalkyl" refers to a saturated, partially saturated, or unsaturated mono- or bicyclic carbon ring that contains 3 to 12 ring atoms, of which one or more —$CH_2$— groups may be optionally replaced with a corresponding number of —C(O)— groups. Illustrative examples of "cycloalkyl" include, but are not limited to, adamantyl, cyclopropyl, cyclobutyl, cyclopentyl, cyclopentenyl, cyclohexyl, cyclohexenyl, indanyl, naphthyl, oxocyclopentyl, 1-oxoindanyl, phenyl, and tetralinyl.

3- to 6-Membered Cycloalkyl—In one aspect, "cycloalkyl" may be "3- to 6-membered cycloalkyl." As used herein, the term "3- to 6-membered cycloalkyl" refers to a saturated, partially saturated, or unsaturated monocyclic carbon ring containing 3 to 6 ring atoms, of which one or more —$CH_2$— groups may be optionally replaced with a corresponding number of —C(O)— groups. Illustrative examples of "3- to 6-membered cycloalkyl" include cyclopropyl, cyclobutyl, cyclopentyl, oxocyclopentyl, cyclopentenyl, cyclohexyl, and phenyl.

Halo—As used herein, the term "halo" includes fluoro, chloro, bromo and iodo. In one aspect, the term "halo" may refer to fluoro, chloro, and bromo. In another aspect, the term "halo" may refer to fluoro and chloro. In another aspect, the term "halo" may refer to fluoro.

Effective Amount—As used herein, the phrase "effective amount" means an amount of a compound or composition which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically-acceptable excipient(s)/carrier(s) utilized, the route of administration, and like factors within the knowledge and expertise of the attending physician.

Pharmaceutically Acceptable—As used herein, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications, commensurate with a reasonable benefit/risk ratio.

In the context of the present invention are encompassed pharmaceutically acceptable salts, complexes, hydrates, solvates, or polymorphs, tautomers, geometrical isomers, optically active forms and pharmaceutically active derivatives of compounds of the invention. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

The term "malaria" includes disease and conditions related to an infection by *Plasmodium*.

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease and/or its symptoms or conditions.

The term "effective amount" includes "prophylaxis-effective amount" as well as "treatment-effective amount".

The term "prophylaxis-effective amount" refers to a concentration of compound of this invention that is effective in inhibiting, decreasing the likelihood of the disease by malarial parasites, or preventing malarial infection or preventing the delayed onset of the disease by malarial parasites, when administered before infection, i.e. before, during and/or slightly after the exposure period to malarial parasites.

The term "prophylaxis" includes causal prophylaxis, i.e. antimalarial activity comprising preventing the pre-erythrocytic development of the parasite, suppressive prophylaxis, i.e. antimalarial activity comprising suppressing the development of the blood stage infection and terminal prophylaxis, i.e. antimalarial activity comprising suppressing the development of intra-hepatic stage infection. This term includes primary prophylaxis (i.e. preventing initial infection) where the antimalarial compound is administered before, during and/or after the exposure period to malarial parasites and terminal prophylaxis (i.e. to prevent relapses or delayed onset of clinical symptoms of malaria) when the antimalarial compound is administered toward the end of and/or slightly after the exposure period to malarial parasites but before the clinical symptoms. Typically, against *P. falciparum* infections, suppressive phophylaxis is used whereas against *P. vivax* or a combination of *P. falciparum* and *P. vivax*, terminal prophylaxis is used.

Likewise, the term "treatment-effective amount" refers to a concentration of compound that is effective in treating malaria infection, e.g. leads to a reduction in parasite numbers in blood following microscopic examination when administered after infection has occurred.

The term "subject" as used herein refers to mammals. For examples, mammals contemplated by the present invention include humans and the like. The compounds discussed herein in many instances may have been named and/or checked with ACD/Name by ACD/Labs® and/or Electronic Lab Notebook by CambridgeSoft®.

Compounds of Formula (I) may form stable pharmaceutically acceptable acid or base salts, and in such cases administration of a compound as a salt may be appropriate. Examples of acid addition salts include acetate, adipate, ascorbate, benzoate, benzenesulfonate, bicarbonate, bisulfate, butyrate, camphorate, camphorsulfonate, choline, citrate, cyclohexyl sulfamate, diethylenediamine, ethanesulfonate, fumarate, glutamate, glycolate, hemisulfate, 2-hydroxyethylsulfonate, heptanoate, hexanoate, hydrochloride, hydrobromide, hydroiodide, hydroxymaleate, lactate, malate, maleate, methanesulfonate, meglumine, 2-naphthalenesulfonate, nitrate, oxalate, pamoate, persulfate, phenylacetate, phosphate, diphosphate, picrate, pivalate, propionate, quinate, salicylate, stearate, succinate, sulfamate, sulfanilate, sulfate, tartrate, tosylate (p-toluenesulfonate), trifluoroacetate, and undecanoate. Examples of base salts include ammonium salts; alkali metal salts such as sodium, lithium and potassium salts; alkaline earth metal salts such as aluminum, calcium and magnesium salts; salts with organic bases such as dicyclohexylamine salts and N-methyl-D-glucamine; and salts with amino acids such as arginine, lysine, ornithine, and so forth. Also, basic nitrogen-containing groups may be quaternized with such agents as: lower alkyl halides, such as methyl, ethyl, propyl, and butyl halides; dialkyl sulfates such as dimethyl, diethyl, and dibutyl; diamyl sulfates; long chain halides such as decyl, lauryl, myristyl and stearyl halides; and arylalkyl halides such as benzyl bromide and others. Non-toxic physiologically-acceptable salts are preferred, although other salts may be useful, such as in isolating or purifying the product.

The salts may be formed by conventional means, such as by reacting the free base form of the product with one or more equivalents of the appropriate acid in a solvent or medium in which the salt is insoluble, or in a solvent such as water, which is removed in vacuo or by freeze drying or by exchanging the anions of an existing salt for another anion on a suitable ion-exchange resin.

Compounds of Formula (I) have one or more chiral centres and/or geometric isomeric centres, and it is to be understood that the invention encompasses all such optical, diastereoisomers, and geometric isomers. The invention further relates to any and all tautomeric forms of the compounds of Formula (I).

It is also to be understood that certain compounds of Formula (I) can exist in solvated as well as unsolvated forms, such as hydrated forms. It is to be understood that the invention encompasses all such solvated forms.

Additional embodiments of the invention are as follows. These additional embodiments relate to compounds of Formula (I) and pharmaceutically acceptable salts thereof. Such specific substituents may be used, where appropriate, with any of the definitions, claims or embodiments defined hereinbefore or hereinafter.

According to a particular aspect, is provided a compound of the invention selected from the following group:

In another aspect, the present invention provides a compound selected from:

N2-(4-cyclopropyl-5-fluoro-6-methyl-2-pyridyl)-5-(4-methylpiperazin-1-yl)-N4-(1-methyltriazol-4-yl)pyrimidine-2,4-diamine;

N2-(4-cyclopropyl-5-fluoro-6-methyl-2-pyridyl)-N4-(1,5-dimethylpyrazol-3-yl)-5-[3-methylpiperazin-1-yl]pyrimidine-2,4-diamine;

N2-(4-cyclopropyl-5-fluoro-6-methyl-2-pyridyl)-N4-(1-ethyl-5-methyl-pyrazol-3-yl)-5-[3-methylpiperazin-1-yl]pyrimidine-2,4-diamine;

N2-(4-cyclopropyl-5-fluoro-6-methyl-2-pyridyl)-5-[3-methyl piperazin-1-yl]-N4-(1-methyltriazol-4-yl)pyrimidine-2,4-diamine;

N2-(5-chloro-4-cyclopropyl-6-methyl-2-pyridyl)-N4-(1,5-dimethylpyrazol-3-yl)-5-[3-methylpiperazin-1-yl]pyrimidine-2,4-diamine;

4-cyclopropyl-6-[[4-[(1,5-dimethylpyrazol-3-yl)amino]-5-[3-methyl piperazin-1-yl]pyrimidin-2-yl]amino]-2-methyl-pyridine-3-carbonitrile;

N4-(1,5-dimethylpyrazol-3-yl)-N2-(4-ethyl-5-fluoro-6-methyl-2-pyridyl)-5-[3-methyl piperazin-1-yl]pyrimidine-2,4-diamine;

N4-(1,5-dimethylpyrazol-3-yl)-N2-(4-ethyl-5-fluoro-6-methyl-2-pyridyl)-5-[(3 S)-3-methylpiperazin-1-yl]pyrimidine-2,4-diamine;

N2-(4-cyclobutyl-5-fluoro-6-methyl-2-pyridyl)-N4-(1,5-dimethylpyrazol-3-yl)-5-[3-methylpiperazin-1-yl]pyrimidine-2,4-diamine;

N2-(5-chloro-4-cyclopropyl-6-methyl-2-pyridyl)-5-[3-methyl piperazin-1-yl]-N4-(2-methyltriazol-4-yl)pyrimidine-2,4-diamine;

N2-(5-chloro-4-cyclopropyl-6-methyl-2-pyridyl)-5-[3-methylpiperazin-1-yl]-N4-(1-methyltriazol-4-yl)pyrimidine-2,4-diamine;

N2-(5-chloro-4-cyclopropyl-6-methyl-2-pyridyl)-5-[(3-methylpiperazin-1-yl]-N4-(2-methyltriazol-4-yl)pyrimidine-2,4-diamine;

N2-(4-cyclopropyl-5-fluoro-6-methyl-2-pyridyl)-5-[3,4-dimethylpiperazin-1-yl]-N4-(1,5-dimethylpyrazol-3-yl)pyrimidine-2,4-diamine;

N2-(4-cyclopropyl-5-fluoro-6-methyl-2-pyridyl)-5-[3,4-dimethylpiperazin-1-yl]-N4-(1-methyltriazol-4-yl)pyrimidine-2,4-diamine; and N2-(4-cyclopropyl-5-fluoro-6-methyl-2-pyridyl)-5-[3,4-dimethyl piperazin-1-yl]-N4-(2-methyltriazol-4-yl)pyrimidine-2,4-diamine; as well as pharmaceutically acceptable salts, complexes, hydrates, solvates, tautomers, polymorphs, racemic mixtures, optically active forms and pharmaceutically active derivative thereof.

According to a particular aspect, compounds of the invention are provided as R enantiomers.

According to a particular aspect, compounds of the invention are provided as S enantiomers or as a racemic mixture.

In another aspect, the present invention provides a compound selected from:

Example 1

N2-(4-cyclopropyl-5-fluoro-6-methyl-2-pyridyl)-5-(4-methylpiperazin-1-yl)-N4-(1-methyltriazol-4-yl)pyrimidine-2,4-diamine;

Example 2

N2-(4-cyclopropyl-5-fluoro-6-methyl-2-pyridyl)-N4-(1,5-dimethylpyrazol-3-yl)-5-[(3R)-3-methylpiperazin-1-yl]pyrimidine-2,4-diamine;

Example 3

N2-(4-cyclopropyl-5-fluoro-6-methyl-2-pyridyl)-N4-(1-ethyl-5-methyl-pyrazol-3-yl)-5-[(3R)-3-methylpiperazin-1-yl]pyrimidine-2,4-diamine;

Example 4

N2-(4-cyclopropyl-5-fluoro-6-methyl-2-pyridyl)-5-[(3R)-3-methyl piperazin-1-yl]-N4-(1-methyltriazol-4-yl)pyrimidine-2,4-diamine;

Example 5

N2-(5-chloro-4-cyclopropyl-6-methyl-2-pyridyl)-N4-(1,5-dimethylpyrazol-3-yl)-5-[(3R)-3-methylpiperazin-1-yl]pyrimidine-2,4-diamine;

Example 6

4-cyclopropyl-6-[[4-[(1,5-dimethylpyrazol-3-yl)amino]-5-[(3R)-3-methyl piperazin-1-yl]pyrimidin-2-yl]amino]-2-methyl-pyridine-3-carbonitrile;

Example 7

N4-(1,5-dimethylpyrazol-3-yl)-N2-(4-ethyl-5-fluoro-6-methyl-2-pyridyl)-5-[(3R)-3-methylpiperazin-1-yl]pyrimidine-2,4-diamine;

Example 8

N4-(1,5-dimethylpyrazol-3-yl)-N2-(4-ethyl-5-fluoro-6-methyl-2-pyridyl)-5-[(3 S)-3-methylpiperazin-1-yl]pyrimidine-2,4-diamine;

Example 9

N2-(4-cyclobutyl-5-fluoro-6-methyl-2-pyridyl)-N4-(1,5-dimethylpyrazol-3-yl)-5-[(3R)-3-methylpiperazin-1-yl]pyrimidine-2,4-diamine;

Example 10

N2-(5-chloro-4-cyclopropyl-6-methyl-2-pyridyl)-5-[(3R)-3-methyl piperazin-1-yl]-N4-(2-methyltriazol-4-yl)pyrimidine-2,4-diamine;

Example 11

N2-(5-chloro-4-cyclopropyl-6-methyl-2-pyridyl)-5-[(3R)-3-methylpiperazin-1-yl]-N4-(1-methyltriazol-4-yl)pyrimidine-2,4-diamine;

Example 12

N2-(5-chloro-4-cyclopropyl-6-methyl-2-pyridyl)-5-[(3R)-3-methyl piperazin-1-yl]-N4-(2-methyltriazol-4-yl)pyrimidine-2,4-diamine;

Example 13

N2-(4-cyclopropyl-5-fluoro-6-methyl-2-pyridyl)-5-[(3R)-3,4-dimethyl piperazin-1-yl]-N4-(1,5-dimethylpyrazol-3-yl)pyrimidine-2,4-diamine;

Example 14

N2-(4-cyclopropyl-5-fluoro-6-methyl-2-pyridyl)-5-[(3R)-3,4-dimethyl piperazin-1-yl]-N4-(1-methyltriazol-4-yl)pyrimidine-2,4-diamine; and

Example 15

N2-(4-cyclopropyl-5-fluoro-6-methyl-2-pyridyl)-5-[(3R)-3,4-dimethyl piperazin-1-yl]-N4-(2-methyltriazol-4-yl)pyrimidine-2,4-diamine; as well as pharmaceutically acceptable salts, complexes, hydrates, solvates, tautomers, polymorphs, racemic mixtures, optically active forms and pharmaceutically active derivative thereof.

According to a further particular embodiment, the present invention provides a compound selected from N2-(4-cyclopropyl-5-fluoro-6-methyl-2-pyridyl)-5-[3,4-dimethyl piperazin-1-yl]-N4-(1,5-dimethylpyrazol-3-yl)pyrimidine-2,4-diamine and its active metabolite N2-(4-cyclopropyl-5-fluoro-6-methyl-2-pyridyl)-N4-(1,5-dimethylpyrazol-3-yl)-5-[3-methyl piperazin-1-yl]pyrimidine-2,4-diamine.

According to another further particular embodiment, the present invention provides a compound N4-(1,5-dimethyl-pyrazol-3-yl)-N2-(4-ethyl-5-fluoro-6-methyl-2-pyridyl)-5-[3-methylpiperazin-1-yl]pyrimidine-2,4-diamine.

According to another further particular embodiment, the present invention provides a compound N2-(5-chloro-4-cyclopropyl-6-methyl-2-pyridyl)-5-[3-methyl piperazin-1-yl]-N4-(2-methyltriazol-4-yl)pyrimidine-2,4-diamine.

Thus, in one aspect there is provided a compound of Formula (I), or a pharmaceutically acceptable salt thereof, for use as a medicament.

The compounds according to the invention may thus be used for the preparation of medicaments, in particular medicaments for inhibiting parasite growth.

Thus, according to another of its aspects, a subject of the invention is medicaments that comprise a compound of Formula (I), or an addition salt of the compound of Formula (I) with a pharmaceutically acceptable acid or base.

These medicaments find their use in therapeutics, especially in the treatment of malaria caused by all species of *plasmodium* such as *P. falciparum, P. vivax, P. malariae, P. ovale* and *P. knowlesi*.

Accordingly, in one aspect, there is provided the use of a compound of Formula (I), or a pharmaceutically acceptable salt thereof, in the manufacture of a medicament for the treatment of a parasitic infection caused by *plasmodium* species in a warm-blooded animal such as a human being.

In another aspect, there is provided the use of a compound of Formula (I), or a pharmaceutically acceptable salt thereof, in the manufacture of a medicament for the production of an antimalarial effect in a warm-blooded animal such as a human being.

In another aspect, there is provided a method for treating a parasitic infection caused by *plasmodium* species in a warm-blooded animal such as a human being, said method including administering to said animal an effective amount of a compound of Formula (I), or a pharmaceutically acceptable salt thereof.

In another aspect, there is provided a method for producing an antimalarial effect in a warm-blooded animal such as a human being, said method including administering to said animal an effective amount of a compound of Formula (I), or a pharmaceutically acceptable salt thereof.

In another aspect, there is provided a compound of Formula (I), or a pharmaceutically acceptable salt thereof, for use in the treatment and/or prophylaxis of malaria in a warm-blooded animal such as a human being.

A compound of Formula (I), or a pharmaceutically acceptable salt thereof, for the therapeutic and prophylactic treatment of mammals including humans, in particular in treating malaria caused by *plasmodium* species, is normally formulated in accordance with standard pharmaceutical practice as a pharmaceutical composition.

Accordingly, in one aspect, there is provided a pharmaceutical composition including a compound of Formula (I), or a pharmaceutically acceptable salt thereof, and at least one pharmaceutically acceptable carrier, diluent, or excipient.

In another aspect, there is provided the use of a pharmaceutical composition including a compound of Formula (I), or a pharmaceutically acceptable salt thereof, in the manufacture of a medicament for the treatment of a parasitic infection caused by *plasmodium* species in a warm-blooded animal such as a human being.

In another aspect, there is provided the use of a pharmaceutical composition including a compound of Formula (I), or a pharmaceutically acceptable salt thereof, in the manufacture of a medicament for the production of an antimalarial effect in a warm-blooded animal such as a human being.

In another aspect, there is provided a method for treating malaria caused by *plasmodium* species in a warm-blooded animal such as a human being, said method including administering to said animal an effective amount of a pharmaceutical composition including a compound of Formula (I), or a pharmaceutically acceptable salt thereof.

In another aspect, there is provided a method for producing an antimalarial effect in a warm-blooded animal such as a human being, said method including administering to said animal an effective amount of a pharmaceutical composition including a compound of Formula (I), or a pharmaceutically acceptable salt thereof.

In another aspect, there is provided a pharmaceutical composition including a compound of Formula (I), or a pharmaceutically acceptable salt thereof, for use in treating malaria caused by *plasmodium* species in a warm-blooded animal such as a human being.

In another aspect, there is provided a pharmaceutical composition including a compound of Formula (I), or a pharmaceutically acceptable salt thereof, for use in the production of an antimalarial effect in a warm-blooded animal such as a human being.

Pharmaceutical Compositions

In some aspects, the invention provides a pharmaceutical composition comprising a compound of Formula (I), or a pharmaceutically acceptable salt thereof, and a pharmaceutically acceptable diluent or carrier.

The language "pharmaceutically acceptable" includes compounds, materials, compositions, and/or dosage forms which are, within the scope of sound medical judgment, suitable for use in contact with the tissues of human beings and animals without excessive toxicity, irritation, allergic response, or other problems or complications, commensurate with a reasonable benefit/risk ratio.

The compounds of Formula (I) may form stable pharmaceutically acceptable acid or base salts, and in such cases administration of a compound as a salt may be appropriate.

Examples of acid addition salts include acetate, adipate, ascorbate, benzoate, benzenesulfonate, bicarbonate, bisulfate, butyrate, camphorate, camphorsulfonate, choline, citrate, cyclohexyl sulfamate, diethylenediamine, ethanesulfonate, fumarate, glutamate, glycolate, hemisulfate, 2-hydroxyethylsulfonate, heptanoate, hexanoate, hydrochloride, hydrobromide, hydroiodide, hydroxymaleate, lactate, malate, maleate, methanesulfonate, meglumine, 2-naphthalenesulfonate, nitrate, oxalate, pamoate, persulfate, phenylacetate, phosphate, diphosphate, picrate, pivalate, propionate, quinate, salicylate, stearate, succinate, sulfamate, sulfanilate, sulfate, tartrate, tosylate (p-toluenesulfonate), trifluoroacetate, and undecanoate. Examples of base salts include ammonium salts; alkali metal salts such as sodium, lithium and potassium salts; alkaline earth metal salts such as aluminum, calcium and magnesium salts; salts with organic bases such as dicyclohexylamine salts and N10 methyl-D-glucamine; and salts with amino acids such as arginine, lysine, ornithine, and so forth. Also, basic nitrogen-containing groups may be quaternized with such agents as: lower alkyl halides, such as methyl, ethyl, propyl, and butyl halides; dialkyl sulfates such as dimethyl, diethyl, and dibutyl; diamyl sulfates; long chain halides such as decyl, lauryl, myristyl and stearyl halides; and arylalkyl halides such as benzyl bromide and others. Non-toxic physiologically acceptable salts are preferred, although other salts may be useful, such as in isolating or purifying the product.

The salts may be formed by conventional means, such as by reacting the free base form of the product with one or more equivalents of the appropriate acid in a solvent or medium in which the salt is insoluble, or in a solvent such as water, which is removed in vacuo or by freeze drying or by exchanging the anions of an existing salt for another anion on a suitable ion-exchange resin.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients well-known in the art. Thus, compositions intended for oral use may contain, for example, one or more coloring, sweetening, flavoring and/or preservative agents.

Suitable pharmaceutically acceptable excipients for a tablet formulation include, for example, inert diluents such as lactose, sodium carbonate, calcium phosphate or calcium carbonate; granulating and disintegrating agents such as corn starch, alginic acid, potato starch or sodium starch glycollate; binding agents such as starch; lubricating agents such as magnesium stearate, stearic acid or talc, polyethylene glycol, and silica; preservative agents such as ethyl or propyl p-hydroxybenzoate; and antioxidants, such as ascorbic acid. Tablet formulations may be uncoated or coated either to modify their disintegration and the subsequent absorption of the active ingredient within the gastrointestinal tract, or to improve their stability and/or appearance, in either case using conventional coating agents and procedures well known in the art.

For example, tablets and capsules for oral administration may further contain conventional excipients including, but not limited to, fillers, disintegrants and wetting agents. Fillers include, but are not limited to, lactose, sugar, microcrystalline cellulose, maize starch, calcium phosphate, and sorbitol.

Binding agents include, but are not limited to, syrup, acacia, gelatin, sorbitol, tragacanth, mucilage of starch and polyvinylpyrrolidone.

Tablets may be coated according to methods well known in the art. For example, tablets and capsules for oral administration may contain conventional excipients including, but not limited to, binding agents, fillers, lubricants, disintegrants and wetting agents.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form or in the form of nano or micronized particles together with one or more suspending agents, such as sodium carboxymethylcellulose, methylcellulose, hydroxypropyl methylcellulose, sodium alginate, polyvinylpyrrolidone, gum tragacanth and gum acacia, or dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, such as ethyl or propyl_p-hydroxybenzoate; antioxidants such as ascorbic acid); coloring agents; flavoring agents; and/or sweetening agents such as sucrose, saccharine or aspartame.

Oily suspensions may be formulated by suspending the active ingredient in a vegetable oil such as *arachis* oil, olive oil, sesame oil or coconut oil or in a mineral oil such as liquid paraffin. The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an antioxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the form of oil-in-water emulsions. The oily phase may be a vegetable oil, such as olive oil or *arachis* oil, or a mineral oil, such as liquid paraffin, or a mixture of any of these. Suitable emulsifying agents may be, for example, naturally-occurring gums such as gum acacia or gum tragacanth, naturally-occurring phosphatides such as soya bean, lecithin, esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurized aerosol arranged to dispense the active ingredient as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

Compositions for administration may also be formulated as a liposome preparation. The liposome preparation can comprise liposomes which penetrate the cells of interest or stratum corneum, and fuse with the cell membrane, resulting in delivery of the contents of the liposome into the cell. Other suitable formulations can employ niosomes. Niosomes are lipid vesicles similar to liposomes, with membranes consisting largely of nonionic lipids, some forms of which are effective for transporting compounds across the stratum corneum.

Compositions for administration may also be formulated as a depot preparation, which may administered by implantation or by intramuscular injection. The compositions may be formulated with suitable polymeric or hydrophobic material (as an emulsion in acceptable oil), ion exchange resins, or sparingly soluble derivatives.

The compound of this invention can also be administered in sustained release forms or from sustained release drug delivery systems.

For further information on formulation, drug delivery and processing techniques, the reader is referred to Remington's Pharmaceutical Sciences (21$^{st}$ Edition, 2005, University of the Sciences in Philadelphia, Lippincott William & Wilkins, or *The Science and Practice of Pharmacy (Remington: The Science & Practice of Pharmacy)*, 22$^{nd}$ Edition, 2012, Loyd Allen (ed.), Pharmaceutical Press which is incorporated herein by reference).

The amount of active ingredient that is combined with one or more excipients to produce a single dosage form will necessarily vary depending upon the host treated and the particular route of administration. For example, a formulation intended for oral administration to humans will generally contain from 0.5 mg to 4 g of active agent compounded with an appropriate and convenient amount of excipients which may vary from about 5 to about 98 percent by weight of the total composition. Dosage unit forms will generally contain about 1 mg to about 500 mg of an active ingredient. For further information on routes of administration and dosage regimes, the reader is referred to Chapter 25.3 in Volume 5 of Comprehensive Medicinal Chemistry (Corwin Hansch; Chairman of Editorial Board), Pergamon Press 1990 and *Remington's Pharmaceutical Sciences*, supra).

As stated above the size of the dose required for the therapeutic or prophylactic treatment of a particular disease state will necessarily vary depending on the host treated, the route of administration and the severity of the illness being treated. Preferably a daily dose in the range of 1-25 mg/kg is employed. Accordingly, the optimum dosage may be determined by the practitioner who is treating any particular patient.

In any of the pharmaceutical compositions, processes, methods, uses, medicaments, and manufacturing features mentioned herein, any of the alternate aspects of the compounds of the invention described herein also apply.

Route of Administration

Compositions of this invention may be administered in any manner, including, but not limited to, orally, parenterally, sublingually, transdermally, vaginally, rectally, transmucosally, topically, via inhalation, via buccal or intranasal administration, or combinations thereof. The compositions of this invention may also be administered in the form of an implant, which allows the slow release of the compositions as well as slow controlled i.v. infusion. In a preferred embodiment, triaminopyrimidine derivatives according to the invention are administered orally.

In a particular embodiment, compounds of the invention are administered at a dose to humans of between about 1 mg and 1,500 mg such as about 200 to 700 mg. In a further particular embodiment, compounds of the invention are administered at a dose of less than 600 mg (e.g. from about 260 mg to about 520 mg).

This invention is further illustrated by the following examples that are not intended to limit the scope of the invention in any way.

The dosage administered, as single or multiple, to an individual will vary depending upon a variety of factors, including the pharmacokinetic properties, patient conditions and characteristics (sex, age, body weight, health, size), extent of symptoms, concurrent treatments, frequency of treatment and the effect desired.

Combinations

The compounds of the invention described herein may be applied as a sole therapy or may involve, in addition to a compound of the invention, one or more other substances and/or treatments. Such co-treatment may be achieved by way of the simultaneous, sequential or separate administration of the individual components of the treatment. Where the administration is sequential or separate, the delay in administering the second component should not be such as to lose the beneficial effect of the combination.

According to a particular embodiment of the invention, the compounds of the invention and pharmaceutical formulations thereof can be administered in combination with a co-agent useful in the treatment of malaria.

Suitable classes and substances include one or more antimalarial agents useful in the treatment and prevention of malaria such as artemisinin or an artemisinin derivative (such as artemether or dihydroartemisinin), chloroquinine, mefloquine, quinine, atoquone/proguanil, doxycycline, hydroxychloroquinine, halofantrine, pyronaridine, lumefantrine, pyrmethamine-sulfadoxine and piperaquine.

Also included are amodiaquine, atovaquone, proguanil hydrochloride, Spiro[3H-indole-3,1'-[1H]pyrido[3,4-b]indol]-2(1H)-one (CAS Registry Number: 1193314-23-6), 5,7'-dichloro-6'-fluoro-2',3',4',9'-tetrahydro-3'-methyl-,(1'R,3'S)-], Sulfur, [4-[[2-(1,1-difluoroethyl)-5-methyl[1,2,4]triazolo[1,5-a]pyrimidin-7-yl]amino]phenyl] pentafluoro-] (CAS Registry Number: 1282041-94-4), Morpholine, and 4-[2-(4-cis-dispiro[cyclohexane-1,3'-[1,2,4]trioxolane-5',2''-tricyclo[3.3.1.13,7]decan]-4-yl phenoxy)ethyl]-] (CAS Registry Number: 1029939-86-3).

Further co-agents useful in the context of the invention are selected from quinacrine, primaquine, tafenaquine, doxycycline, ferroquine, and arterolane.

The invention encompasses the administration of at least one compound of the invention according to the invention or of a pharmaceutical formulation thereof, wherein the compound of the invention or the pharmaceutical formulation thereof is administered to an individual prior to, simultaneously or sequentially with other therapeutic regimens or co-agents useful in the treatment of malaria (e.g. multiple drug regimens), in an effective amount. Compounds of the invention or pharmaceutical formulations thereof that are administered simultaneously with said co-agents can be administered in the same or different composition(s) and by the same or different route(s) of administration.

Patients

In an embodiment, patients according to the invention are suffering from malaria.

In another embodiment, patients according to the invention are patients with a high risk of being infected by *Plasmodium*.

In another embodiment, patients according to the invention are patients with a high risk of being infected by *Plasmodium falciparum*.

In another embodiment, patients according to the invention are patients with a high risk of being infected by *Plasmodium vivax*.

Use According to the Invention

In one embodiment, the invention provides a use of a compound according to Formula (I) as described herein, as well as pharmaceutically acceptable salts, hydrates, solvates, polymorphs, tautomers, geometrical isomers, or optically active forms thereof, for the preparation of a pharmaceutical composition for the treatment or prophylaxis of malaria.

In another embodiment, the invention provides a method for preventing or treating malaria in a patient. The method comprises administering an effective amount of a compound according to the invention, or a pharmaceutically acceptable salt or a pharmaceutically active derivative thereof or a pharmaceutical formulation thereof, to a patient in need thereof.

In another embodiment, the invention provides a compound according to the invention, as well as pharmaceutically acceptable salts or a pharmaceutically active derivative thereof or a pharmaceutical formulation thereof, for use in the treatment or prophylaxis of malaria.

In another embodiment, the invention provides a use of a compound of the invention or a method according to the invention wherein the compound of the invention is to be administered in combination with a co-agent useful in the treatment of malaria.

In another embodiment, the invention provides a pharmaceutical composition comprising a compound of the invention in combination with a co-agent useful in the treatment of malaria.

The compounds and compositions of this invention may be used in a method for inactivating parasitic infection in a cell comprising the step of contacting the cell with an effective amount of at least one compound according to the invention. According to a particular aspect, the cell is a primate cell, for example a human cell, such as a red blood cell.

Process

In another embodiment, the invention provides a process for the preparation of an compound of Formula (I) comprising the step of reacting a derivative according to Formula (IV) with a derivative of Formula (V) to lead to an intermediate of Formula (X) under palladium catalysed amination conditions (e.g. using 9,9-Dimethyl-4,5-bis(diphenylphosphino)xanthene and Tris(dibenzylideneacetone) dipalladium as a catalyst) as follows:

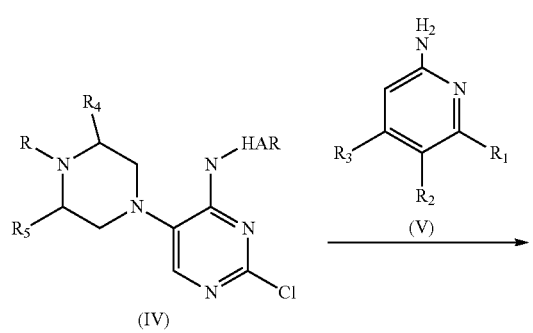

(IV)

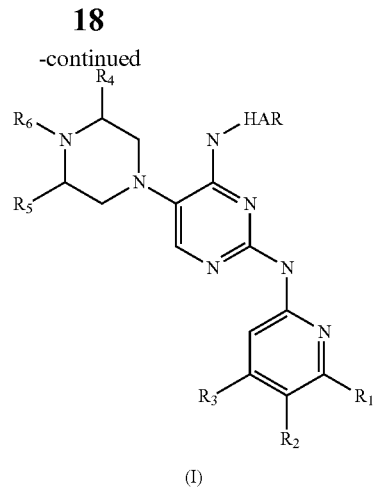

(I)

wherein R is a protecting group (e.g. Boc).

In a further optional step the compounds of Formula (I) where $R_6$=H are further converted under reductive amination conditions to a further compound of Formula (I) wherein $R_6$=alkyl.

In another embodiment, the invention provides a process for the preparation of a compound of Formula (I) comprising the step of reacting a derivative according to Formula (IV) with a derivative of Formula (V) to lead to an intermediate of Formula (X) under palladium catalysed amination conditions (e.g. using 9,9-Dimethyl-4,5-bis(diphenylphosphino)xanthene and Tris(dibenzylideneacetone) dipalladium as a catalyst) as follows:

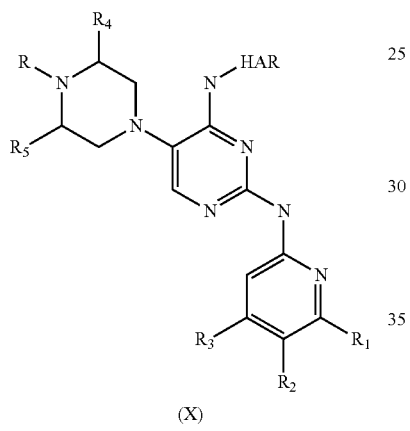

(X)

wherein R is a protecting group (e.g. Boc).

In another embodiment, the invention provides a process for the preparation of a compound of Formula (I) comprising the step of reacting a derivative according to Formula (X) to lead to a compound of Formula (I) under acidic conditions (e.g. 4N hydrochloric acid or trifluoro acetic acid) as follows:

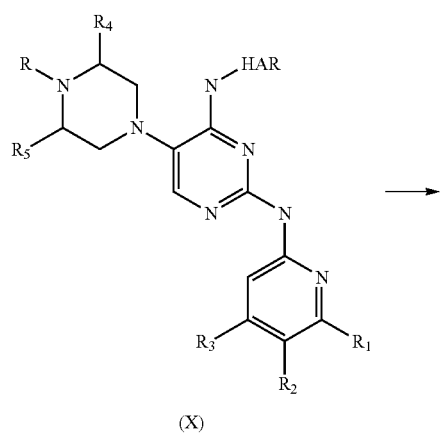

(X)

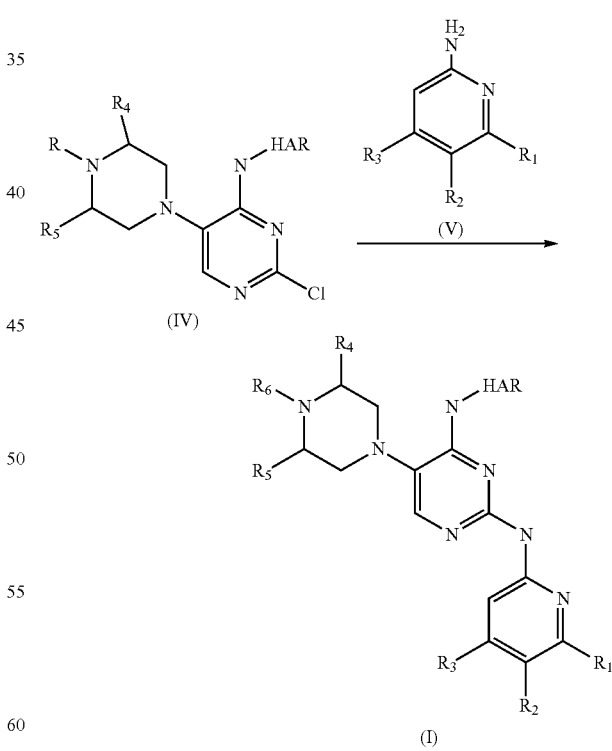

(I)

wherein R is $R^6$ and $R^6$ is alkyl.

In another embodiment, the invention provides an intermediate of Formula (IV) wherein $R^4$, $R^5$ and HAR are as defined herein and R is selected from a protecting group (e.g. Boc) and $R^6$:

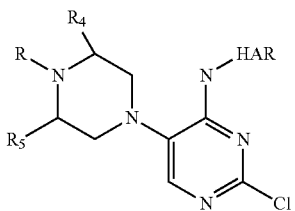

(IV)

In another embodiment, the invention provides an intermediate of Formula (IV) selected from the following group:
tert-butyl 4-(2-chloro-4-((1,5-dimethyl-1H-pyrazol-3-yl)amino)pyrimidin-5-yl)-2-methyl piperazine-1-carboxylate;
tert-butyl4-(2-chloro-4-((1-ethyl-5-methyl-1H-pyrazol-3-yl)amino)pyrimidin-5-yl)-2-methylpiperazine-1-carboxylate;
tert-butyl4-(2-chloro-4-((2-methyl-2H-1,2,3-triazol-4-yl)amino)pyrimidin-5-yl)-2-methylpiperazine-1-carboxylate;
tert-butyl 4-(2-chloro-4-((1-methyl-1H-1,2,3-triazol-4-yl)amino)pyrimidin-5-yl)-2-methylpiperazine-1-carboxylate; and
2-chloro-N-(1-methyl-1H-1,2,3-triazol-4-yl)-5-(4-methylpiperazin-1-yl)pyrimidin-4-amine.

In another embodiment, the invention provides an intermediate of Formula (X) wherein $R^1$, $R^2$, R3 $R^4$, $R^5$ and HAR are as defined herein and R is a protecting group (e.g. Boc):

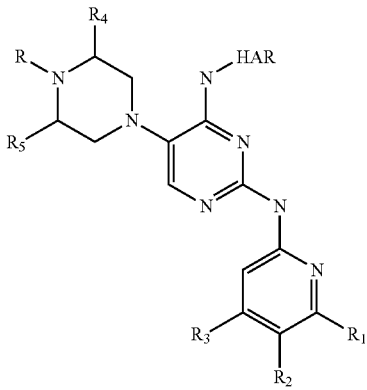

(X)

In another embodiment, the invention provides an intermediate of Formula (X) selected from the following group:
tert-butyl 4-(2-((4-cyclopropyl-5-fluoro-6-methylpyridin-2-yl)amino)-4-((1,5-dimethyl-1H-pyrazol-3-yl)amino)pyrimidin-5-yl)-2-methylpiperazine-1-carboxylate;
tert-butyl4-(2-((4-cyclopropyl-5-fluoro-6-methylpyridin-2-yl)amino)-4-((1-ethyl-5-methyl-1H-pyrazol-3-yl)amino)pyrimidin-5-yl)-2-methylpiperazine-1-carboxylate;
tert-butyl4-(2-((4-cyclopropyl-5-fluoro-6-methylpyridin-2-yl)amino)-4-((1-methyl-1H-1,2,3-triazol-4-yl)amino)pyrimidin-5-yl)-2-methylpiperazine-1-carboxylate;
tert-butyl 4-(2-((5-chloro-4-cyclopropyl-6-methylpyridin-2-yl)amino)-4-((1,5-dimethyl-1H-pyrazol-3-yl)amino)pyrimidin-5-yl)-2-methylpiperazine-1-carboxylate;
tert-butyl 4-(2-((5-cyano-4-cyclopropyl-6-methylpyridin-2-yl)amino)-4-((1,5-dimethyl-1H-pyrazol-3-yl)amino)pyrimidin-5-yl)-2-methylpiperazine-1-carboxylate;
tert-butyl 4-(4-((1,5-dimethyl-1H-pyrazol-3-yl)amino)-2-((4-ethyl-5-fluoro-6-methylpyridin-2-yl)amino)pyrimidin-5-yl)-2-methylpiperazine-1-carboxylate;
tert-butyl 4-(4-((1,5-dimethyl-1H-pyrazol-3-yl)amino)-2-((4-ethyl-5-fluoro-6-methylpyridin-2-yl)amino)pyrimidin-5-yl)-2-methylpiperazine-1-carboxylate;
tert-butyl 4-(2-((4-cyclobutyl-5-fluoro-6-methylpyridin-2-yl)amino)-4-((1,5-dimethyl-1H-pyrazol-3-yl)amino)pyrimidin-5-yl)-2-methylpiperazine-1-carboxylate;
tert-butyl4-(2-((5-chloro-4-cyclopropyl-6-methylpyridin-2-yl)amino)-4-((2-methyl-2H-1,2,3-triazol-4-yl)amino)pyrimidin-5-yl)-2-methylpiperazine-1-carboxylate;
tert-butyl 4-(2-((5-chloro-4-cyclopropyl-6-methylpyridin-2-yl)amino)-4-((1-methyl-1H-1,2,3-triazol-4-yl)amino)pyrimidin-5-yl)-2-methylpiperazine-1-carboxylate; and
tert-butyl 4-(2-((3-cyclopropyl-4-fluoro-5-methylphenyl)amino)-4-((2-methyl-2H-1,2,3-triazol-4-yl)amino)pyrimidin-5-yl)-2-methylpiperazine-1-carboxylate.

If not commercially available, the necessary starting materials for the procedures such as those described herein may be made by procedures which are selected from standard organic chemical techniques, techniques which are analogous to the synthesis of known, structurally similar compounds, or techniques which are analogous to the described procedure or the procedures described in the Examples.

It is noted that many of the starting materials for synthetic methods as described herein are commercially available and/or widely reported in the scientific literature, or could be made from commercially available compounds using adaptations of processes reported in the scientific literature. The reader is further referred to *Advanced Organic Chemistry*, 5th Edition, by Jerry March and Michael Smith, published by John Wiley & Sons 2001, for general guidance on reaction conditions and reagents.

It will also be appreciated that in some of the reactions mentioned herein it may be necessary/desirable to protect any sensitive groups in compounds. The instances where protection is necessary or desirable are known to those skilled in the art, as are suitable methods for such protection. Conventional protecting groups may be used in accordance with standard practice (for illustration see T. W. Greene, *Protective Groups in Organic Synthesis*, published by John Wiley and Sons, 1991) and as described hereinabove.

EXAMPLES

The invention is now illustrated by, but not limited to, the following Examples, for which, unless otherwise stated:
(i) evaporations were carried out by rotary evaporation in vacuo and work-up procedures were carried out after removal of residual solids by filtration;
(ii) temperatures are quoted as ° C.; operations were carried out at room temperature, that is typically in the range of 18-26° C. and without the exclusion of air unless otherwise stated, or unless the skilled person would otherwise work under an inert atmosphere;
(iii) column chromatography (by the flash procedure) was used to purify compounds and was performed on Merck Kieselgel silica (Art. 9385) unless otherwise stated;
(iv) in general, the course of reactions was followed by TLC, HPLC, or LC/MS and reaction times are given for illustration only; yields are given for illustration only and are not necessarily the maximum attainable;
(v) the structure of the end-products of the invention was generally confirmed by NMR and mass spectral techniques. Proton magnetic resonance spectra were generally determined in DMSO-$d_6$ unless otherwise stated, using a Bruker DRX-300 spectrometer or a Bruker DRX-400 spectrometer, operating at a field strength of 300 MHz, or 400 MHz, respectively. In cases where the NMR spectrum is complex, only diagnostic signals are reported. Chemical shifts are reported in parts per million downfield from tetramethylsilane as an external standard (δ scale) and peak multiplicities are shown thus: s, singlet; d, doublet; dd, doublet of doublets; dt, doublet of triplets; dm, doublet of multiplets; t, triplet; m, multiplet; br, broad. Fast-atom bombardment (FAB) mass spectral data were generally obtained using a Platform spectrometer (supplied by Micromass) run in electrospray and, where appropriate, either positive ion data or negative ion data were collected or using Agilent 1100 series LC/MS equipped with Sedex 75ELSD, and where appropriate, either positive ion data or negative ion data were collected. The lowest mass major ion is reported for molecules where isotope splitting results in multiple mass spectral peaks (for example when chlorine is present). Reverse Phase HPLC was carried out using YMC Pack ODS-AQ (100×20 mmID, S-5μ particle size, 12 nm pore size) on Agilent instruments;

(vi) each intermediate was purified to the standard required for the subsequent stage and was characterized in sufficient detail to confirm that the assigned structure was correct; purity was assessed by HPLC, TLC, or NMR and identity was determined by infra-red spectroscopy (IR), mass spectroscopy or NMR spectroscopy as appropriate; and (vii) the following abbreviations may be used:
ACN—acetonitrile; TLC—thin layer chromatography; HPLC—high pressure liquid chromatography; MPLC—medium pressure liquid chromatography; NMR—nuclear magnetic resonance spectroscopy; DMA—Dimethylacetamide- DMSO—dimethylsulfoxide; $CDCl_3$-deuterated chloroform; MeOD—deuterated methanol, i.e. $D_3COD$; MS—mass spectroscopy; ESP (or ES)—electrospray; HBSS—Hank's balanced salt solution; EI—electron impact; APCI—atmospheric pressure chemical ionization; THF—tetrahydrofuran; DCM—dichloromethane; HPMC—Hydroxypropyl Methylcellulose; MeOH—methanol; DMF—dimethylformamide; EtOAc—ethyl acetate; LC/MS—liquid chromatography/mass spectrometry; h—hour(s); min is minute(s); d—day(s); MTBD—N-methyl-1,5,7-triazabicyclo[4.4.0] dec-5-ene; NADPH—Nicotinamide adenine dinucleotide phosphate—reduced form; PEG—Polyethylene Glycol; RT—room temperature; TEER—Trans epithelial electric resistance; TFA—trifluoroacetic acid; v/v—ratio of volume/ volume; Boc denotes t-butoxycarbonyl; Cbz denotes benzyloxycarbonyl; Bz denotes benzoyl; atm denotes atmospheric pressure; rt denotes room temperature; mg denotes milligram; g denotes gram; μL denotes microliter; mL denotes milliliter; L denotes liter; μM denotes micromolar; mM denotes millimolar; M denotes molar; N denotes normal; nm denotes nanometer.

In accordance with the invention, the compounds of generic Formula (I) may be prepared according to the processes that follow. The synthesis of the intermediates (II-Xk) and compounds of generic formula (I) are described in Schemes 1, 2 and 3.

Synthetic scheme 1

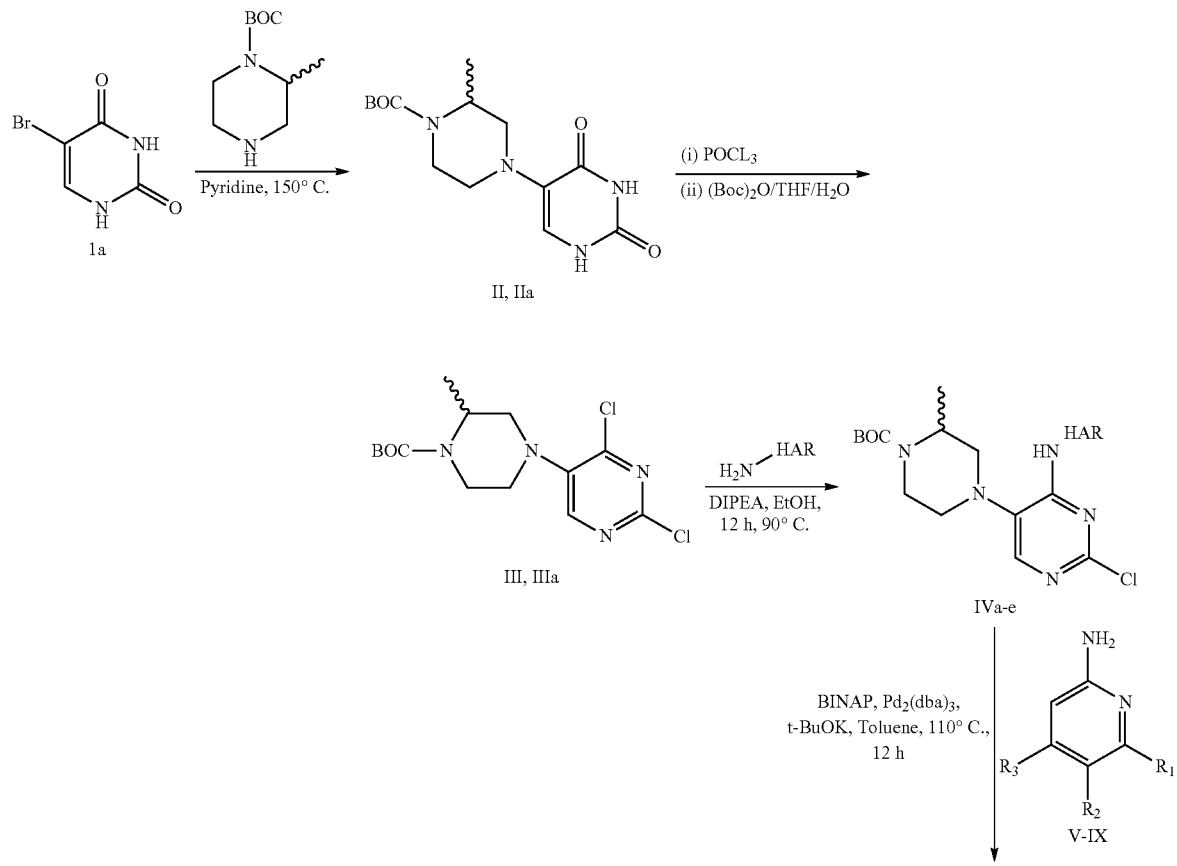

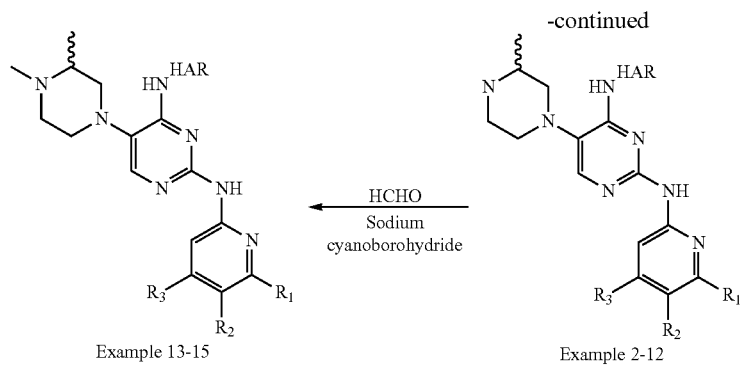
Example 13-15 ← HCHO, Sodium cyanoborohydride — Example 2-12 ← 4N HCl in dioxane — Xa-k
HAR is: (1,5-dimethyl-1H-pyrazol-3-yl) or (1-ethyl-5-methyl-1H-pyrazol-3-yl) or (2-methyl-2H-1,2,3-triazol-4-yl) or (1-methyl-1H-1,2,3-triazol-4-yl)
Synthetic scheme 2
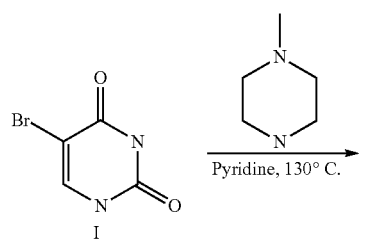
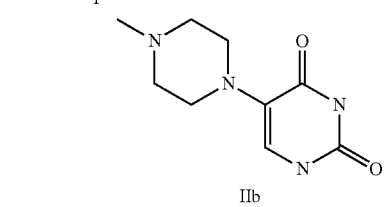
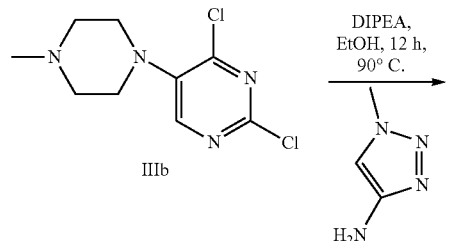
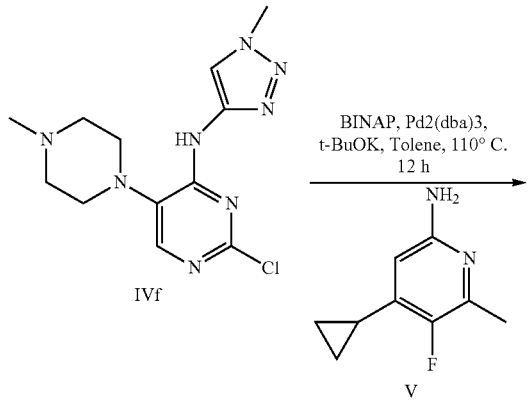
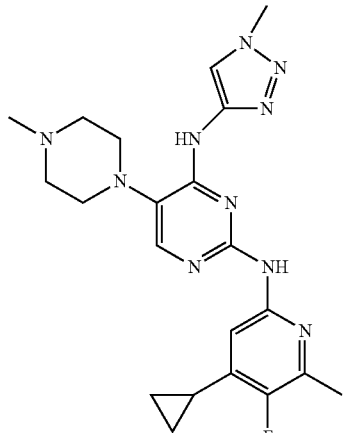
Example 1
Synthetic scheme 3
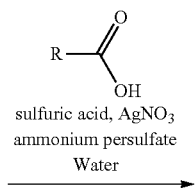
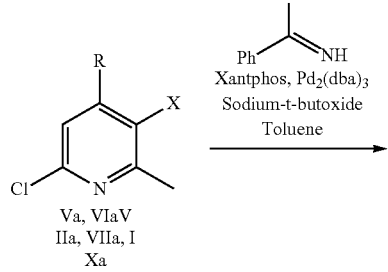

-continued

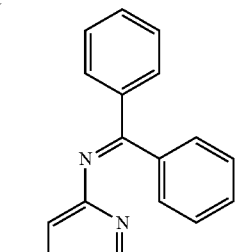

Vb, VIb, VIIb, VIIIb, IXb

↓ 4N HCl in Dioxane

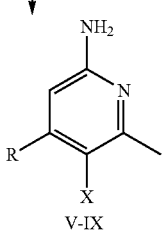

V-IX

R = Ethyl, cyclopropyl and cyclobutyl
X = F, Cl, CN

Intermediate II (R)-tert-butyl-4-(2,4-dioxo-1,2,3,4-tetrahydropyrimidin-5-yl)-2-methylpiperazine-1-carboxylate

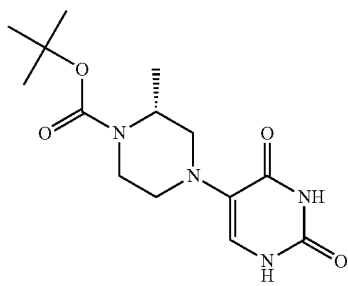 [SMILES: C[C@@H]1CN(c2c[nH]c(=O)[nH]c2=O)CCN1C(=O)OC(C)(C)C]

In a Biotage microwave vial, 5-bromopyrimidine-2,4(1H,3H)-dione (Ia) (24 g, 125.67 mmol, Aldrich) and (R)-tert-butyl 2-methylpiperazine-1-carboxylate (37.8 g, 188.50 mmol, Activate Scientific) were taken in pyridine (12 mL) and irradiated at 150° C. for 90 min. Pyridine was removed under vacuum and residue was poured in water to get the suspension, which was filtered and vacuum dried to get solid of (R)-tert-butyl-4-(2,4-dioxo-1,2,3,4-tetrahydropyrimidin-5-yl)-2-methylpiperazine-1-carboxylate (22.00 g, 56.4%). Note: Reaction was done in 12 batches of 2 g each. All combined and work up was done. $^1$H NMR (300 MHz, DMSO-d6) δ ppm 1.19 (d, J=6.78 Hz, 3H) 1.40 (s, 9H) 2.30 (d, J=2.83 Hz, 1H) 2.42 (dd, J=11.30, 3.58 Hz, 1H) 2.93-3.22 (m, 3H) 3.72 (d, J=13.19 Hz, 1H) 4.12 (br. s., 1H) 6.73 (d, J=4.71 Hz, 1H) 10.51 (br. s., 1H) 11.10 (s, 1H) MS (ES$^+$), (M+H)$^+$=310.09 for $C_{14}H_{22}N_4O_4$.

Intermediate IIa (S)-tert-butyl-4-(2,4-dioxo-1,2,3,4-tetrahydropyrimidin-5-yl)-2-methylpiperazine-1-carboxylate

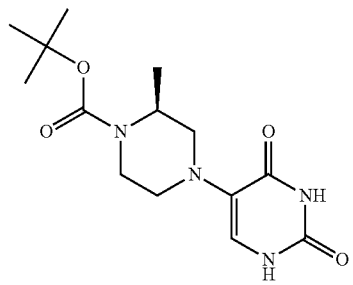 [SMILES: C[C@H]1CN(c2c[nH]c(=O)[nH]c2=O)CCN1C(=O)OC(C)(C)C]

Intermediate IIa was prepared from 5-bromopyrimidine-2,4(1H,3H)-dione (Aldrich) and (S)-tert-butyl 2-methylpiperazine-1-carboxylate (Activate Scientific) using a procedure analogous to Intermediate II. $^1$H NMR (300 MHz, DMSO-d6) δ ppm 1.19 (d, J=6.78 Hz, 3H) 1.40 (s, 9H) 2.30 (d, J=2.83 Hz, 1H) 2.42 (dd, J=11.30, 3.58 Hz, 1H) 2.93-3.22 (m, 3H) 3.72 (d, J=13.19 Hz, 1H) 4.12 (br. s., 1H) 6.73 (d, J=4.71 Hz, 1H) 10.51 (br. s., 1H) 11.10 (s, 1H) MS (ES$^+$), (M+H)$^+$=310.09 for $C_{14}H_{22}N_4O_4$.

Intermediate III (R)-tert-butyl 4-(2,4-dichloropyrimidin-5-yl)-2-methylpiperazine-1-carboxylate

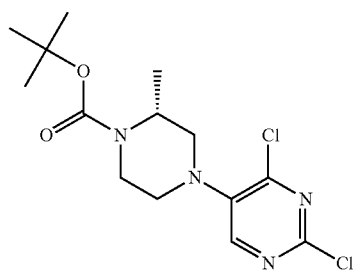 [SMILES: C[C@@H]1CN(c2cnc(Cl)nc2Cl)CCN1C(=O)OC(C)(C)C]

In a 2 L round-bottom flask, (R)-tert-butyl 4-(2,4-dioxo-1,2,3,4-tetrahydropyrimidin-5-yl)-2-methylpiperazine-1-carboxylate (22 g, 70.89 mmol, Intermediate II) taken in phosphorus oxychloride (793 ml, 8506.56 mmol) to give a brown suspension. The reaction mixture was refluxed for 5-6 h, reaction was monitored by LCMS and identified the required mass. Phosphorus oxychloride was distilled out under reduced pressure, the remaining oil was diluted with THF (250 mL) and crushed ice (400 g), and the reaction mixture was basified to pH 8. Di-tert-butyl dicarbonate (22.17 ml, 96.41 mmol, Aldrich) was added to the mixture and stirred for 16 h at rt. The reaction mixture was diluted with methanol and filtered it off to remove excess salt. The solvent was removed under vacuum and residue was diluted with water (50 mL) and extracted with ethyl acetate (500 mL×3). Organic layers were dried over sodium sulphate and solvent was removed under reduced pressure. The residue was loaded on silica gel and purified to obtain solid of (R)-tert-butyl 4-(2,4-dichloropyrimidin-5-yl)-2-methylpiperazine-1-carboxylate (23.00 g, 93%). $^1$H NMR (300 MHz, CDCl$_3$) δ ppm 1.31 (d, J=6.78 Hz, 3H) 1.37-1.47 (m, 9H) 2.70-2.93 (m, 2H) 3.15-3.29 (m, 3H) 3.94 (d, J=13.94 Hz, 1H) 4.33 (br. s., 1H) 8.11 (s, 1H) MS (ES$^+$), (M+H)$^+$=349 for C$_{14}$H$_{20}$Cl$_2$N$_4$O$_2$.

Intermediate IIIa (S)-tert-butyl 4-(2,4-dichloropyrimidin-5-yl)-2-methylpiperazine-1-carboxylate

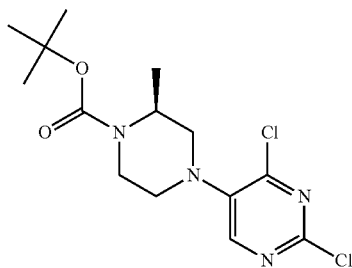 [SMILES: C[C@H]1CN(c2cnc(Cl)nc2Cl)CCN1C(=O)OC(C)(C)C]

Intermediate IIIa was prepared from IIa using a procedure analogous to Intermediate III. $^1$H NMR (300 MHz, CDCl$_3$) δ ppm 1.31 (d, J=6.78 Hz, 3H) 1.37-1.47 (m, 9H) 2.70-2.93 (m, 2H) 3.15-3.29 (m, 3H) 3.94 (d, J=13.94 Hz, 1H) 4.33 (br. s., 1H) 8.11 (s, 1H) MS (ES$^+$), (M+H)$^+$=349 for C$_{14}$H$_{20}$Cl$_2$N$_4$O$_2$.

Intermediate IVa (R)-tert-butyl 4-(2-chloro-4-((1,5-dimethyl-1H-pyrazol-3-yl)amino)pyrimidin-5-yl)-2-methylpiperazine-1-carboxylate

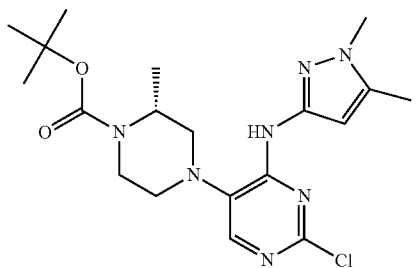 [SMILES: Cc1cc(Nc2nc(Cl)ncc2N2CCN(C(=O)OC(C)(C)C)[C@H](C)C2)nn1C]

In a 25 mL Biotage microwave vial (R)-tert-butyl 4-(2,4-dichloropyrimidin-5-yl)-2-methylpiperazine-1-carboxylate (500 mg, 1.44 mmol, Intermediate III) and 1,5-dimethyl-1H-pyrazol-3-amine (160 mg, 1.44 mmol, Princeton Bio.) was taken in ethanol (10 mL). N,N-diisopropylethylamine (0.754 mL, 4.32 mmol) was added and the reaction mass was subjected to microwave irradiation at 120° C. for 4 hours. The reaction was monitored by LCMS and identified the required mass. Reaction mass was cooled and evaporated to dryness and the residue was then chromatographed with EtoAc/Hexane on silica to get pure solid of (R)-tert-butyl 4-(2-chloro-4-((1,5-dimethyl-1H-pyrazol-3-yl)amino)pyrimidin-5-yl)-2-methylpiperazine-1-carboxylate (300 mg, 49.4%) MS (ES$^+$), (M+H)$^+$=422.20 for C$_{19}$H$_{28}$ClN$_7$O$_2$.

Intermediate IVb (R)-tert-butyl 4-(2-chloro-4-((1-ethyl-5-methyl-1H-pyrazol-3-yl)amino)pyrimidin-5-yl)-2-methylpiperazine-1-carboxylate

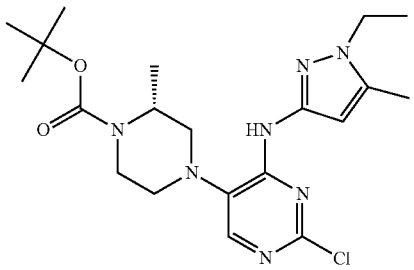 [SMILES: CCn1nc(Nc2nc(Cl)ncc2N2CCN(C(=O)OC(C)(C)C)[C@H](C)C2)cc1C]

Intermediate IVb was prepared from 1-ethyl,5-methyl-1H-pyrazol-3-amine (ChemCollect) and Intermediate III using a procedure analogous to Intermediate IVa. Yield: 63.7%, MS (ES$^+$), (M+H)$^+$=436.38 for C$_{20}$H$_{30}$ClN$_7$O$_2$.

Intermediate IVc (R)-tert-butyl 4-(2-chloro-4-((2-methyl-2H-1,2,3-triazol-4-yl)amino)pyrimidin-5-yl)-2-methylpiperazine-1-carboxylate

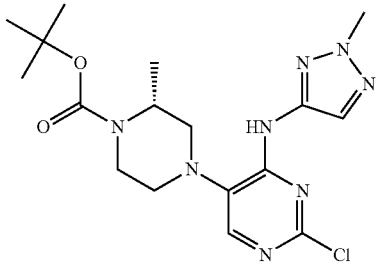 [SMILES: C[C@@H]1CN(c2cnc(Cl)nc2Nc2cnn(C)n2)CCN1C(=O)OC(C)(C)C]

In a 50 ml round bottom flask 2-methyl-2H-1,2,3-triazol-4-amine hydrochloride (388 mg, 2.88 mmol, ChemBridge) was taken in DCM (2 mL) and triethylamine (200 mL, 1.44 mmol) was added under ice cooling and stirred for 5 min. This was evaporated completely to dryness. Residue was dissolved in DMF (10 mL) and cooled using ice bath. Sodium hydride (173 mg, 4.32 mmol) was added and stirred at cold for 15 mins and (R)-tert-butyl 4-(2,4-dichloropyrimidin-5-yl)-2-methylpiperazine-1-carboxylate (500 mg, 1.44 mmol, Intermediate III) was added. The resulting reaction mixture was stirred at RT overnight. Reaction was followed by LCMS and identified required mass. DMF was evaporated and the suspension was then partitioned between water and ethyl acetate. Organic layers were combined, dried over sodium sulphate, concentrated to dryness and purified on combiflash to get (R)-tert-butyl 4-(2-chloro-4-((2-methyl-2H-1,2,3-triazol-4-yl)amino)pyrimidin-5-yl)-2-methylpiperazine-1-carboxylate (180 mg, 30.6%). MS (ES$^+$), (M+H)$^+$=409.36 for C$_{17}$H$_{25}$ClN$_8$O$_2$.

Intermediate IVd (R)-tert-butyl 4-(2-chloro-4-((1-methyl-1H-1,2,3-triazol-4-yl)amino)pyrimidin-5-yl)-2-methylpiperazine-1-carboxylate

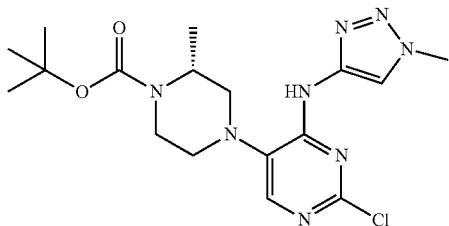 [SMILES: C[C@@H]1CN(c2cnc(Cl)nc2Nc2cn(C)nn2)CCN1C(=O)OC(C)(C)C]

Intermediate IVd was prepared from 1-methyl-1H-1,2,3-triazol-4-amine hydrochloride (ChemBridge) and Intermediate III using a procedure analogous to Intermediate IVc. Yield: 51%. MS (ES+), (M+H)+=409.32 for $C_{17}H_{25}ClN_8O_2$.

Intermediate IVe (S)-tert-butyl 4-(2-chloro-4-((1,5-dimethyl-1H-pyrazol-3-yl)amino)pyrimidin-5-yl)-2-methylpiperazine-1-carboxylate

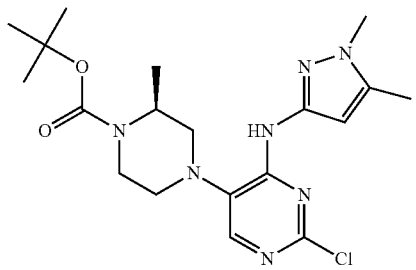 [SMILES: Cc1cc(Nc2nc(Cl)ncc2N2CCN(C(=O)OC(C)(C)C)[C@@H](C)C2)nn1C]

Intermediate IVe was prepared from 1,5-dimethyl-1H-pyrazol-3-amine (160 mg, 1.44 mmol, Princeton Bio.) and Intermediate IIIa using a procedure analogous to Intermediate Iva. Yield: 49%, MS (ES+), (M+H)+=422.20 for $C_{19}H_{28}ClN_7O_2$.

Intermediate IIb 5-(4-methylpiperazin-1-yl)pyrimidine-2,4(1H,3H)-dione

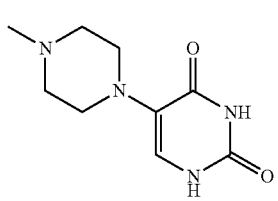

In a 20 mL Biotage microwave vial 5-Bromouracil (3 g, 15.71 mmol, Aldrich) and N-methylpiperazine (2.61 mL, 23.56 mmol, Aldrich) were taken in pyridine (15 mL) to give a white suspension. The vial was then capped and subjected to microwave irradiation for 45 mins at 150° C. The reaction was monitored by LCMS and identified the required mass. Pyridine was removed under vacuum and the residue was then triturated with ethyl acetate and the suspension was filtered off and vacuum dried to get 5-(4-methylpiperazin-1-yl) pyrimidine-2,4(1H,3H)-dione (3.30 g, 100%) as a dark grey solid. $^1$H NMR (300 MHz, DMSO-d6) δ ppm 2.07 (s, 3H) 2.43-2.49 (m, 4H) 2.98-3.09 (m, 4H) 7.21 (s, 1H) 10.84 (br. s., 1H) MS (ES+), (M+H)+=211.09 for $C_9H_{14}N_4O_2$.

Intermediate IIIb 2,4-dichloro-5-(4-methylpiperazin-1-yl)pyrimidine

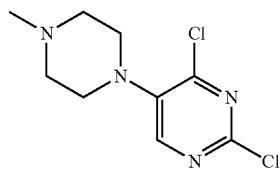

In a 250 mL two neck round-bottomed flask 5-(4-methylpiperazin-1-yl)pyrimidine-2,4(1H,3H)-dione (3.30 g, 15.70 mmol, Intermediate IIb) was taken in phosphorus oxychloride (200 ml, 2145.67 mmol) to give a brown suspension. The reaction mass was then heated to 120° C. for 4 hrs. The reaction was monitored by LCMS and identified the required mass. Phosphorus oxychloride was evaporated under vacuum to get a thick dark residue. Ice was added to it and was neutralized with sodium bicarbonate to pH 8 under cooling. The suspension was then extracted with 10% Methanol in dichloromethane. The organic layer was dried over sodium sulphate and solvent was removed under vacuum to get residue, which was purified on combiflash with Methanol and dichloromethane to get solid of 2,4-dichloro-5-(4-methylpiperazin-1-yl)pyrimidine (1.100 g, 28.4%). $^1$H NMR (300 MHz, CDCl$_3$) δ ppm 2.34-2.38 (s, 3H) 2.52-2.63 (m, 4H) 3.13 (br. s., 4H) 8.64 (s, 1H) MS (ES+), (M+H)+=247 for $C_9H_{12}Cl_2N_4$.

Intermediate IVf 2-chloro-N-(1-methyl-1H-1,2,3-triazol-4-yl)-5-(4-methylpiperazin-1-yl)pyrimidin-4-amine

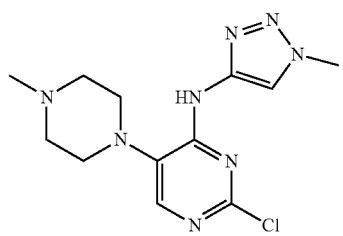

Intermediate IVf was prepared from 1-methyl-1H-1,2,3-triazol-4-amine hydrochloride (ChemBridge) and Intermediate IIIb using a procedure analogous to Intermediate IVc. Yield: 29.5%, MS (ES+), (M+H)+=309.32 for $C_{12}H_{15}ClN_8$.

Intermediate Va 6-chloro-4-cyclopropyl-3-fluoro-2-methylpyridine

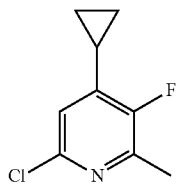

In a 100 ml three necked round bottom flask equipped with condenser and thermometer, solution of sulfuric acid (1.318 mL, 24.73 mmol) in water (45 mL) was taken and to this cyclopropanecarboxylic acid (2.129 g, 24.73 mmol, Aldrich) and Silver nitrate (1.260 g, 7.42 mmol) were added. To the resultant suspension 6-chloro-3-fluoro-2-methylpyridine (1.8 g, 12.37 mmol, Matrix Scientific) was added to give a white suspension. The mixture was heated to 70° C. and then freshly prepared Ammonium persulfate (8.47 g, 37.10 mmol) solution in water (35 mL) was added drop wise for 20 min. After completion of addition, heating source was removed and kept for carbon dioxide evolution. The reaction was monitored by TLC. Then mixture was cooled and worked up with sodium bicarbonate to the neutral pH and the compound was extracted into diethyl ether (3×50 ml). The organic layer was evaporated to obtain crude sample 2.1 g. The crude sample was purified on silica gel using DCM-Hexane to obtain 6-chloro-4-cyclopropyl-3-fluoro-2-methylpyridine (0.540 g, 23.53%). $^1$H NMR (300 MHz, DMSO-$d_6$) δ ppm 0.87-0.95 (m, 2H) 1.05-1.15 (m, 2H) 2.00-2.12 (m, 1H) 2.38 (d, J=3.20 Hz, 3H) 6.96 (d, J=4.71 Hz, 1H) MS (ES$^+$), (M+H)$^+$=186.05 for $C_9H_9ClFN$.

Intermediate Vb 4-cyclopropyl-N-(diphenylmethylene)-5-fluoro-6-methylpyridin-2-amine

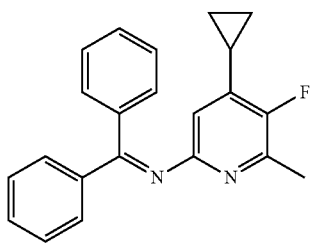 [SMILES: Cc1nc(N=C(c2ccccc2)c2ccccc2)cc(C2CC2)c1F]

6-chloro-4-cyclopropyl-3-fluoro-2-methylpyridine (Intermediate Va, 532 mg, 2.87 mmol) was taken in a 25 ml thermal reactor and was dissolved in Toluene (10 mL). Benzenemethanimine, alpha-phenyl- (0.721 mL, 4.30 mmol, Aldrich), racemic-2,2'-Bis(diphenylphosphino)-1,1'-binaphthyl (71.4 mg, 0.11 mmol, Aldrich), Palladium (II) acetate (25.7 mg, 0.11 mmol, Aldrich) and Cesium carbonate (1401 mg, 4.30 mmol) were added into this and the resulting mixtures was refluxed at 120° C. under nitrogen for overnight. Reaction was monitored with LCMS and showed product formation. Resultant mass was concentrated and purified over combiflash followed by gilson HPLC to get pure yellow gum of 4-cyclopropyl-N-(diphenylmethylene)-5-fluoro-6-methylpyridin-2-amine (350 mg, 37.0%). $^1$H NMR (300 MHz, DMSO-$d_6$) δ ppm 0.44-0.55 (m, 2H) 0.82-1.02 (m, 2H) 1.81-1.96 (m, 1H) 2.25 (d, J=3.20 Hz, 3H) 5.98 (d, J=4.90 Hz, 1H) 7.10 (dd, J=6.59, 2.83 Hz, 2H) 7.28-7.37 (m, 3H) 7.44-7.60 (m, 3H) 7.62-7.71 (m, 2H) MS (ES$^+$), (M+H)$^+$=331.40 for $C_{22}H_{19}FN_2$.

Intermediate V 4-cyclopropyl-5-fluoro-6-methylpyridin-2-amine hydrochloride

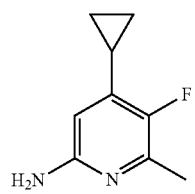

In a 50 mL round-bottom flask 4-cyclopropyl-N-(diphenylmethylene)-5-fluoro-6-methylpyridin-2-amine (350 mg, 1.06 mmol) was taken in 1,4-dioxane (10 mL) colorless solution. HCl in Dioxane (4 ml, 16.00 mmol) was added slowly at rt. Reaction mass was stirred at RT for 2 h and showed the reaction was completed, which was confirmed by LCMS. Reaction mass was concentrated and triturated with acetonitrile to get white solid of 4-cyclopropyl-5-fluoro-6-methylpyridine-2-amine (200 mg, 93%) as a hydrochloride salt. $^1$H NMR (300 MHz, DMSO-$d_6$) δ ppm 0.77-0.92 (m, 2H) 1.14-1.27 (m, 2H) 1.97-2.18 (m, 1H) 2.37 (d, J=3.01 Hz, 3H) 6.33 (d, J=5.84 Hz, 1H) 7.49 (br. s., 2H) 14.19 (br. s., 1H) MS (ES$^+$), (M+H)$^+$=167.12 for $C_9H_{11}FN_2$.

Intermediate VIa6-chloro-4-ethyl-3-fluoro-2-methylpyridine

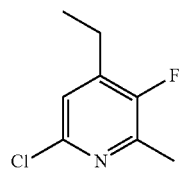

Intermediate VIa was prepared from 6-chloro-3-fluoro-2-methylpyridine (Matrix Scientific) and propionic acid using a procedure analogous to Intermediate Va. Yield: 50.5% $^1$H NMR (300 MHz, DMSO-$d_6$) δ ppm 1.18 (t, J=7.54 Hz, 3H) 2.26 (d, J=1.13 Hz, 3H) 2.63-2.81 (m, 2H) 7.36 (d, J=4.71 Hz, 1H). MS (ES$^+$), (M+H)$^+$=174.12 for $C_8H_9ClFN$.

Intermediate VIb

N-(diphenylmethylene)-4-ethyl-5-fluoro-6-methyl-pyridin-2-amine

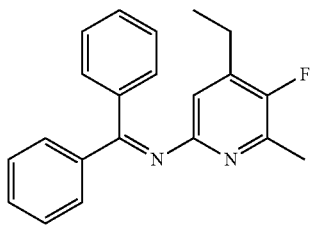 [SMILES: CCc1cc(N=C(c2ccccc2)c2ccccc2)nc(C)c1F]

Intermediate VIb was prepared from Intermediate VIa using a procedure analogous to Intermediate Vb. Yield: 28% $^1$H NMR (300 MHz, DMSO-d$_6$) δ ppm 1.18 (t, J=7.54 Hz, 3H) 2.26 (d, J=1.13 Hz, 3H) 2.63-2.81 (m, 2H) 5.98 (d, J=4.90 Hz, 1H) 7.10 (dd, J=6.59, 2.83 Hz, 2H) 7.28-7.37 (m, 3H) 7.44-7.60 (m, 3H) 7.62-7.71 (m, 2H) MS (ES$^+$), (M+H)$^+$=319.12 for C$_{21}$H$_{19}$FN$_2$.

Intermediate VI 4-ethyl-5-fluoro-6-methylpyridin-2-amine hydrochloride

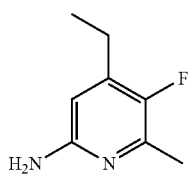

Intermediate VI was prepared from Intermediate VIb using a procedure analogous to Intermediate V. Yield: 94%, $^1$H NMR (300 MHz, DMSO-d$_6$) δ ppm 1.18 (t, J=7.54 Hz, 3H) 2.26 (d, J=1.13 Hz, 3H) 2.63-2.81 (m, 2H) 7.36 (d, J=4.71 Hz, 1H). MS (ES$^+$), (M+H)$^+$=155.06 for C$_8$H$_{11}$FN$_2$.

Intermediate VIIa 6-chloro-4-cyclopropyl-2-methylnicotinonitrile

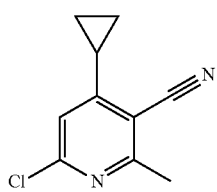

Intermediate VIIa was prepared from 6-chloro-2-methyl-nicotinonitrile (Manchester Organics) and propionic acid using a procedure analogous to Intermediate Va. Yield: 14%, MS (ES$^+$), (M+H)$^+$=193.10 for C$_{10}$H$_9$ClN$_2$.

Intermediate VIIb 4-cyclopropyl-6-((diphenylmethylene)amino)-2-methylnicotinonitrile

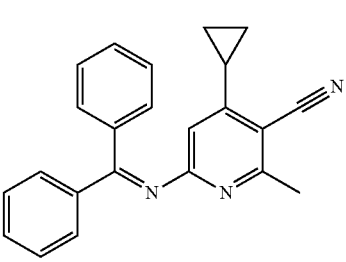 [SMILES: Cc1nc(N=C(c2ccccc2)c2ccccc2)cc(C2CC2)c1C#N]

Intermediate VIIb was prepared from Intermediate VIIa using a procedure analogous to Intermediate Vb. Yield: 81% MS (ES$^+$), (M+H)$^+$=338.40 for C$_{23}$H$_{19}$N$_3$.

Intermediate VII 6-amino-4-cyclopropyl-2-methylnicotinonitrile hydrochloride

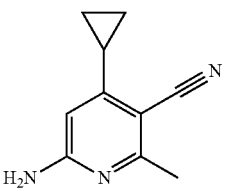

Intermediate VII was prepared from Intermediate VIIb using a procedure analogous to Intermediate V. Yield: 38.6%, MS (ES$^+$), (M+H)$^+$=174.14 for C$_{10}$H$_{11}$N$_3$.

Intermediate VIIIa 6-chloro-4-cyclobutyl-3-fluoro-2-methylpyridine

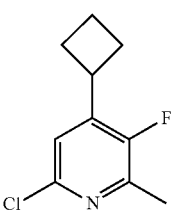

Intermediate VIIIa was prepared from 6-chloro-3-fluoro-2-methylpyridine (Matrix Scientific) and cyclobutanecarboxylic acid using a procedure analogous to Intermediate Va. Yield: 21%, MS (ES$^+$), (M+H)$^+$=200 for C$_{10}$H$_{11}$ClFN.

Intermediate VIIIb 4-cyclobutyl-N-(diphenylmethylene)-5-fluoro-6-methylpyridin-2-amine

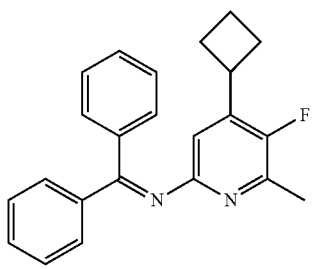 [SMILES: Cc1nc(N=C(c2ccccc2)c2ccccc2)cc(C2CCC2)c1F]

Intermediate VIIIb was prepared from Intermediate VIIIa using a procedure analogous to Intermediate Vb. Yield: 40%, MS (ES$^+$), (M+H)$^+$=346 for $C_{23}H_{21}FN_2$.

Intermediate VIII 4-cyclobutyl-5-fluoro-6-methylpyridin-2-amine hydrochloride

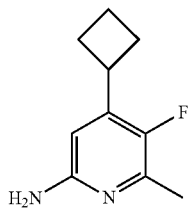

Intermediate VIII was prepared from Intermediate VIIIb using a procedure analogous to Intermediate V. Yield: 88%, $^1$H NMR (300 MHz, DMSO-d$_6$) δ ppm 1.73-1.92 (m, 1H) 1.98-2.17 (m, 3H) 2.21-2.33 (m, 2H) 2.33-2.38 (m, 3H) 3.58-3.75 (m, 1H) 6.72 (d, J=5.65 Hz, 1H) 7.74 (br. s., 1H) MS (ES$^+$), (M+H)$^+$=167.12 for $C_{10}H_{13}FN_2$.

Intermediate IXc 3,6-dichloro-2-methylpyridine

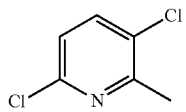

To a suspension of 5-chloro-6-methylpyridin-2-amine (7.5 g, 52.60 mmol, Combi-Blocks) in DCM (200 mL) was added copper(II) chloride (9.19 g, 68.38 mmol) and stirred for 10 min. Tert-butyl nitrite (12.50 mL, 105.20 mmol) was added and the stirring was continued for a further 30 min at RT. The color changed to dark blue. The reaction was monitored by LCMS. LCMS showed the completion of the reaction. The reaction mixture was washed with water and brine solution, and the organic layer was dried on sodium sulphate and concentrated under vacuum to get crude. The product was purified by column chromatography using 5% ethyl acetate:hexane mixture to get 3,6-dichloro-2-methylpyridine (3.80 g, 44.6%) as a yellow liquid. MS (ES$^+$), (M+H)$^+$=162.15 for $C_6H_5Cl_2N$.

Intermediate IXa 3,6-dichloro-4-cyclopropyl-2-methylpyridine

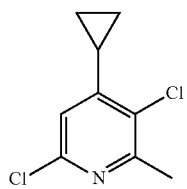

Intermediate IXa was prepared from Intermediate IXc using a procedure analogous to Intermediate Va. Yield: 23%, MS (ES$^+$), (M+H)$^+$=202.24 for $C_9H_9Cl_2N$.

Intermediate IXb 5-chloro-4-cyclopropyl-N-(diphenylmethylene)-6-methylpyridin-2-amine

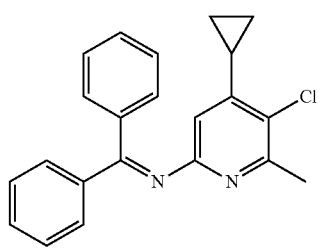 [SMILES: Cc1nc(N=C(c2ccccc2)c2ccccc2)cc(C2CC2)c1Cl]

In a 100 ml RBF 3,6-dichloro-4-cyclopropyl-2-methylpyridine (250 mg, 1.24 mmol), Benzenemethanimine, alpha-phenyl- (0.228 mL, 1.36 mmol) and 9,9-Dimethyl-4,5-bis(diphenylphosphino)xanthene (57.3 mg, 0.10 mmol) was taken in toluene (6 mL) and the reaction mixture degassed for 5 min. Then Tris(dibenzylidene acetone)dipalladium(0) (45.3 mg, 0.05 mmol) and Sodium tert-butoxide (357 mg, 3.71 mmol) were added. The RM was then heated at 110° C. for 3 h under nitrogen. The reaction was monitored by LCMS and identified the required mass. RM was filtered off on a celite bed. Acetic acid (40 µL, 2 eq) was added to the filtrate. The filtrate was then adsorbed on silica and chromatographed with ethyl acetate/hexane to get 5-chloro-4-cyclopropyl-N-(diphenylmethylene)-6-methylpyridine-2-amine (300 mg, 69.9%) as a solid. MS (ES$^+$), (M+H)$^+$= 347.59 for $C_{22}H_9ClN_2$.

Intermediate IX 5-chloro-4-cyclopropyl-6-methylpyridin-2-amine hydrochloride

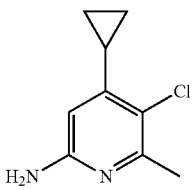

Intermediate IX was prepared from Intermediate IXb using a procedure analogous to Intermediate V. Yield: 48%, MS (ES+), (M+H)+=183.45 for $C_9H_{11}ClN_2$.

Intermediate Xa (R)-tert-butyl 4-(2-((4-cyclopropyl-5-fluoro-6-methylpyridin-2-yl)amino)-4-((1,5-dimethyl-1H-pyrazol-3-yl)amino)pyrimidin-5-yl)-2-methylpiperazine-1-carboxylate

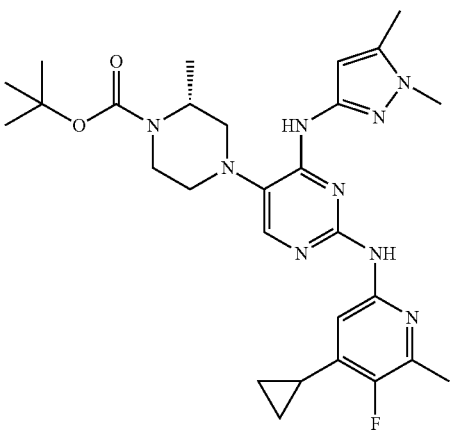 [SMILES: Cc1nc(Nc2ncc(N3CCN(C(=O)OC(C)(C)C)[C@H](C)C3)c(Nc3cc(C)n(C)n3)n2)cc(C2CC2)c1F]

(R)-tert-butyl 4-(2-chloro-4-((1,5-dimethyl-1H-pyrazol-3-yl)amino)pyrimidin-5-yl)-2-methylpiperazine-1-carboxylate (185 mg, 0.44 mmol, Intermediate IVa) was taken in a 50 ml thermal reactor and was dissolved in toluene (10 mL). 4-cyclopropyl-5-fluoro-6-methylpyridin-2-amine hydrochloride (89 mg, 0.44 mmol, Intermediate V), 9,9-Dimethyl-4,5-bis(diphenylphosphino)xanthene (25.4 mg, 0.04 mmol), Tris(di benzylideneacetone)dipalladium(0) (20.08 mg, 0.02 mmol) and Sodium tert-butoxide (84 mg, 0.88 mmol) were added into this and the resulting mixture was refluxed at 120° C. under nitrogen overnight. Reaction was monitored with LCMS and identified required mass. Reaction mixture was cooled and diluted with methanol and filtered through Celite bed and resultant filtrate was concentrated and purified over combiflash followed by Gilson preparative HPLC to get pure white solid of (R)-tert-butyl 4-(2-((4-cyclopropyl-5-fluoro-6-methylpyridin-2-yl)amino)-4-((1,5-dimethyl-1H-pyrazol-3-yl)amino)pyrimidin-5-yl)-2-methylpiperazine-1-carboxylate (60.0 mg, 24.81%). MS (ES+), (M+H)+=552.37 for $C_{28}H_{38}FN_9O_2$.

Intermediate Xb (R)-tert-butyl 4-(2-((4-cyclopropyl-5-fluoro-6-methylpyridin-2-yl)amino)-4-((1-ethyl-5-methyl-1H-pyrazol-3-yl)amino)pyrimidin-5-yl)-2-methylpiperazine-1-carboxylate

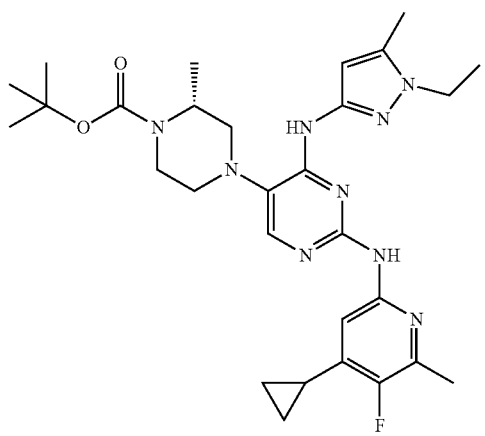 [SMILES: CCn1nc(Nc2nc(Nc3cc(C4CC4)c(F)c(C)n3)ncc2N2CCN(C(=O)OC(C)(C)C)[C@H](C)C2)cc1C]

This was prepared as described above for Intermediate Xa from Intermediate IVb and Intermediate V. Yield: 23.12%, MS (ES+), (M+H)+=567.60 for $C_{29}H_{40}FN_9O_2$.

Intermediate Xc (R)-tert-butyl 4-(2-((4-cyclopropyl-5-fluoro-6-methylpyridin-2-yl)amino)-4-((1-methyl-1H-1,2,3-triazol-4-yl)amino)pyrimidin-5-yl)-2-methylpiperazine-1-carboxylate

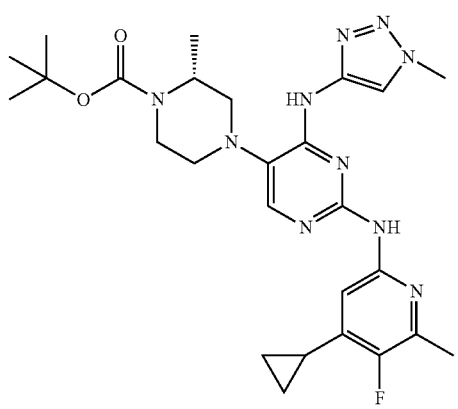 [SMILES: Cc1nc(Nc2ncc(N3CCN(C(=O)OC(C)(C)C)[C@H](C)C3)c(Nc3cn(C)nn3)n2)cc(C2CC2)c1F]

This was prepared as described above for Intermediate Xa from Intermediate IVd and Intermediate V. Yield: 45.5%, MS (ES+), (M+H)+=539.44 for $C_{26}H_{35}FN_{10}O_2$.

Intermediate Xd (R)-tert-butyl 4-(2-((5-chloro-4-cyclopropyl-6-methylpyridin-2-yl)amino)-4-((1,5-dimethyl-1H-pyrazol-3-yl)amino)pyrimidin-5-yl)-2-methylpiperazine-1-carboxylate

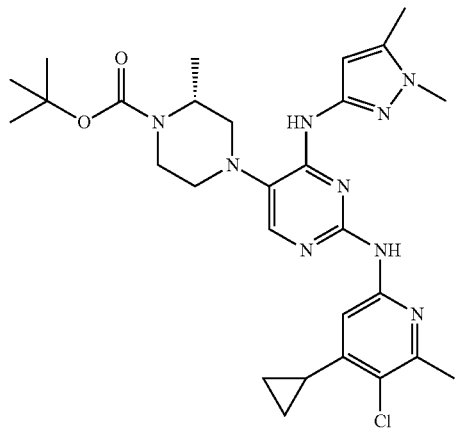

This was prepared as described above for Intermediate Xa from Intermediate IVa and Intermediate IX. Yield: 44.6%, MS (ES+), (M+H)+=569.39 for $C_{28}H_{38}ClN_9O_2$.

Intermediate Xe (R)-tert-butyl 4-(2-((5-cyano-4-cyclopropyl-6-methylpyridin-2-yl)amino)-4-((1,5-dimethyl-1H-pyrazol-3-yl)amino)pyrimidin-5-yl)-2-methylpiperazine-1-carboxylate

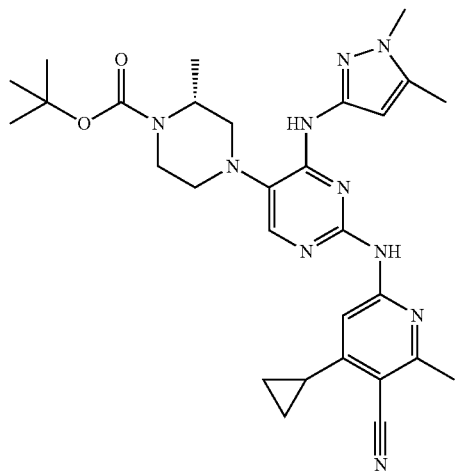 [SMILES: Cc1nc(Nc2ncc(N3CCN(C(=O)OC(C)(C)C)[C@H](C)C3)c(Nc3cc(C)n(C)n3)n2)cc(C2CC2)c1C#N]

This was prepared as described above for Intermediate Xa from Intermediate IVa and Intermediate VII. Yield: 35.5%, MS (ES+), (M+H)+=559.35 for $C_{29}H_{38}N_{10}O_2$.

Intermediate Xf (R)-tert-butyl 4-(4-((1,5-dimethyl-1H-pyrazol-3-yl)amino)-2-((4-ethyl-5-fluoro-6-methylpyridin-2-yl)amino)pyrimidin-5-yl)-2-methylpiperazine-1-carboxylate

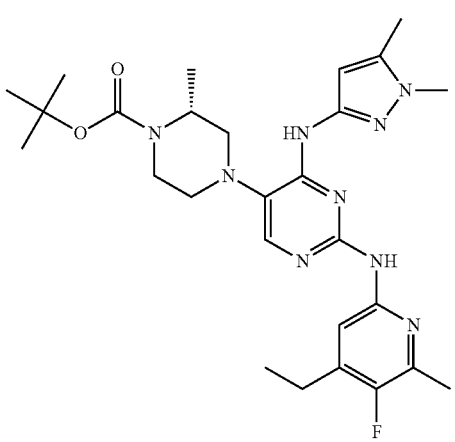 [SMILES: CCc1cc(Nc2ncc(N3CCN(C(=O)OC(C)(C)C)[C@H](C)C3)c(Nc3cc(C)n(C)n3)n2)nc(C)c1F]

This was prepared as described above for Intermediate Xa from Intermediate IVa and Intermediate VI. Yield: 57.9%, MS (ES+), (M+H)+=540.21 for $C_{27}H_{38}FN_9O_2$.

Intermediate Xg (S)-tert-butyl 4-(4-((1,5-dimethyl-1H-pyrazol-3-yl)amino)-2-((4-ethyl-5-fluoro-6-methylpyridin-2-yl)amino)pyrimidin-5-yl)-2-methylpiperazine-1-carboxylate

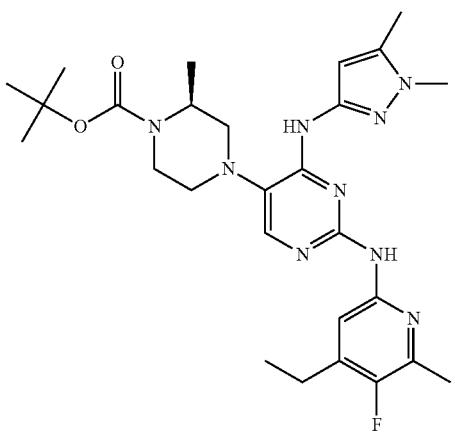 [SMILES: CCc1cc(Nc2ncc(N3CCN(C(=O)OC(C)(C)C)[C@@H](C)C3)c(Nc3cc(C)n(C)n3)n2)nc(C)c1F]

This was prepared as described above for Intermediate Xa from Intermediate IVe and Intermediate VI. Yield: 57.9%, MS (ES+), (M+H)+=540.21 for $C_{27}H_{38}FN_9O_2$.

Intermediate Xh (R)-tert-butyl 4-(2-((4-cyclobutyl-5-fluoro-6-methyl-pyridin-2-yl)amino)-4-((1,5-dimethyl-1H-pyrazol-3-yl)amino)pyrimidin-5-yl)-2-methylpiperazine-1-carboxylate (72.0 mg, 25.6%)

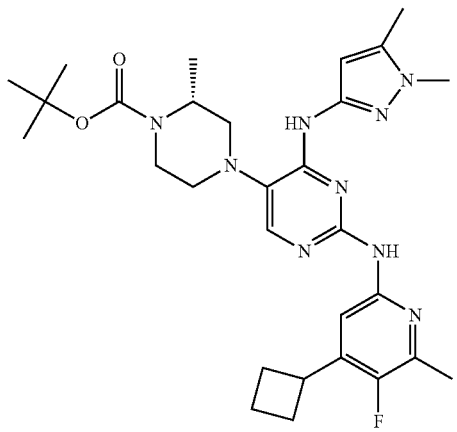 [SMILES: Cc1nc(Nc2ncc(N3CCN(C(=O)OC(C)(C)C)[C@H](C)C3)c(Nc3cc(C)n(C)n3)n2)cc(C2CCC2)c1F]

This was prepared as described above for Intermediate Xa from Intermediate IVa and Intermediate VIII. Yield: 25.6%, MS (ES$^+$), (M+H)$^+$=566.33 for $C_{29}H_{40}FN_9O_2$.

Intermediate Xi (R)-tert-butyl 4-(2-((5-chloro-4-cyclopropyl-6-methylpyridin-2-yl)amino)-4-((2-methyl-2H-1,2,3-triazol-4-yl)amino)pyrimidin-5-yl)-2-methylpiperazine-1-carboxylate

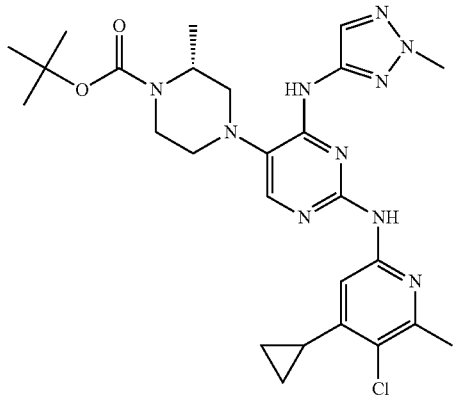 [SMILES: Cc1nc(Nc2ncc(N3CCN(C(=O)OC(C)(C)C)[C@H](C)C3)c(Nc3cnn(C)n3)n2)cc(C2CC2)c1Cl]

This was prepared as described above for Intermediate Xa from Intermediate IVc and Intermediate IX. Yield: 46.0%, MS (ES$^+$), (M+H)$^+$=555.26 for $C_{26}H_{35}ClN_{10}O_2$.

Intermediate Xj (R)-tert-butyl 4-(2-((5-chloro-4-cyclopropyl-6-methylpyridin-2-yl)amino)-4-((1-methyl-1H-1,2,3-triazol-4-yl)amino)pyrimidin-5-yl)-2-methylpiperazine-1-carboxylate

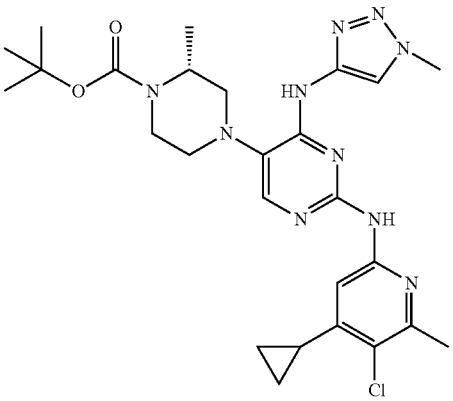

This was prepared as described above for Intermediate Xa from Intermediate IVd and Intermediate IX. Yield: 14.75%, MS (ES$^+$), (M+H)$^+$=555.26 for $C_{26}H_{35}ClN_{10}O_2$.

Intermediate Xk (R)-tert-butyl 4-(2-((3-cyclopropyl-4-fluoro-5-methylphenyl)amino)-4-((2-methyl-2H-1,2,3-triazol-4-yl)amino)pyrimidin-5-yl)-2-methylpiperazine-1-carboxylate

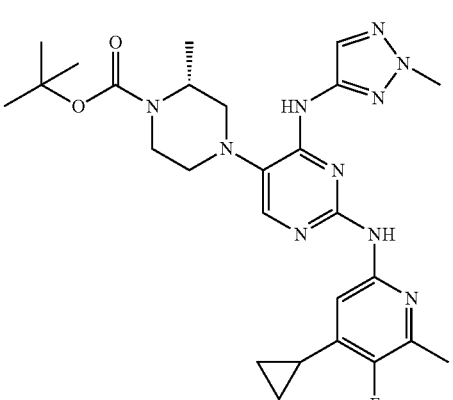

This was prepared as described above for Intermediate Xa from Intermediate IVc and Intermediate V. Yield: 58.3%, MS (ES$^+$), (M+H)$^+$=539.29 for $C_{26}H_{35}FN_{10}O_2$.

Example 1

N2-(4-cyclopropyl-5-fluoro-6-methylpyridin-2-yl)-N4-(1-methyl-1H-1,2,3-triazol-4-yl)-5-(4-methylpiperazin-1-yl)pyrimidine-2,4-diamine

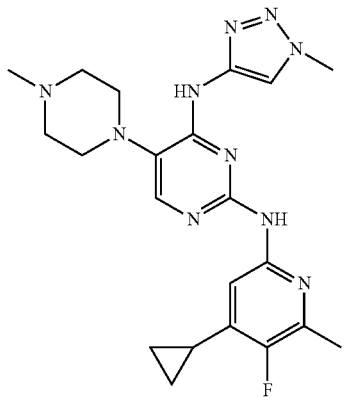

This was prepared as described above for Intermediate Xa from Intermediate IVf and Intermediate V. Yield: 21.28%, $^1$H NMR (300 MHz, DMSO-d6) δ ppm 0.70-0.82 (m, 2H) 1.04-1.15 (m, 2H) 1.99-2.14 (m, 1H) 2.26 (s, 3H) 2.36 (d, J=3.01 Hz, 3H) 2.87 (t, J=4.43 Hz, 4H) 4.05 (s, 3H) 6.55 (s, 1H) 7.85 (d, J=5.09 Hz, 1H) 8.07 (s, 1H) 8.51 (s, 1H) 8.94 (s, 1H) 9.62 (s, 1H). MS (ES$^+$), (M+H)$^+$=439 for $C_{21}H_{27}FN_{10}$.

Example 2

(R)—N2-(4-cyclopropyl-5-fluoro-6-methylpyridin-2-yl)-N4-(1,5-dimethyl-1H-pyrazol-3-yl)-5-(3-methylpiperazin-1-yl)pyrimidine-2,4-diamine dihydrochloride

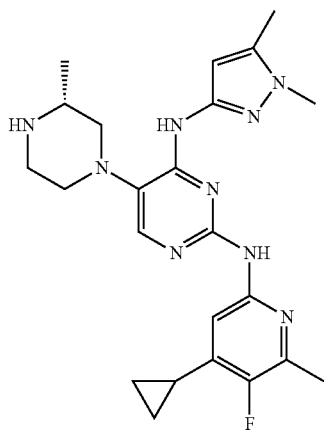 [SMILES: Cc1nc(Nc2ncc(N3CCN[C@H](C)C3)c(Nc3cc(C)n(C)n3)n2)cc(C2CC2)c1F]

In a 50 mL round-bottom flask, (R)-tert-butyl 4-(2-((4-cyclopropyl-5-fluoro-6-methylpyridin-2-yl)amino)-4-((1,5-dimethyl-1H-pyrazol-3-yl)amino)pyrimidin-5-yl)-2-methylpiperazine-1-carboxylate (55 mg, 0.10 mmol, Intermediate Xa) was taken in 1,4-dioxane (10 mL) colorless solution. 4N HCl in Dioxane (4 ml, 16.00 mmol) was added slowly at rt. Reaction mass was stirred at RT for 2 h and showed the reaction was completed, which was confirmed by LCMS. Reaction mass was concentrated and triturated with acetonitrile to get white solid of (R)—N2-(4-cyclopropyl-5-fluoro-6-methylpyridin-2-yl)-N4-(1,5-dimethyl-1H-pyrazol-3-yl)-5-(3-methylpiperazin-1-yl)pyrimidine-2,4-diamine (40.0 mg, 76%) $^1$H NMR (300 MHz, DMSO-d$_6$) δ ppm 0.73-0.82 (m, 2H) 1.15-1.22 (m, 2H) 1.29 (d, J=6.22 Hz, 3H) 2.13 (t, J=4.71 Hz, 1H) 2.31 (s, 3H) 2.54 (d, J=3.20 Hz, 3H) 2.76-2.89 (m, 1H) 2.95-3.18 (m, 3H) 3.25-3.38 (m, 1H) 3.42 (br. s., 1H) 3.56-3.80 (m, 4H) 6.64-6.89 (m, 2H) 8.12 (s, 1H) 9.38 (br. s., 1H) 9.81 (br. s., 1H) 10.29 (s, 1H) 11.39 (br. s., 1H) 13.93 (br. s., 1H) MS (ES$^+$), (M+H)$^+$= 452.27 for $C_{23}H_{30}FN_9$.

Example 3

(R)—N2-(4-cyclopropyl-5-fluoro-6-methylpyridin-2-yl)-N4-(1-ethyl-5-methyl-1H-pyrazol-3-yl)-5-(3-methylpiperazin-1-yl)pyrimidine-2,4-diamine dihydrochloride

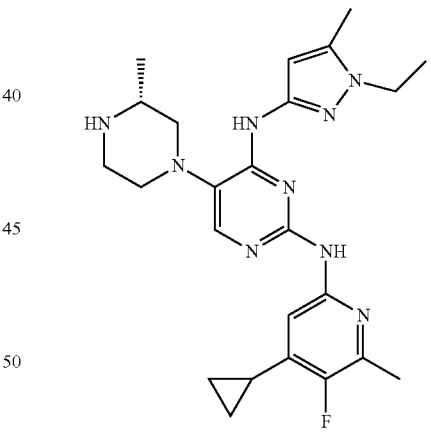

This was prepared as described above for Example 2 from Intermediate Xb. Yield: 96%, $^1$H NMR (300 MHz, DMSO-d$_6$) δ ppm 0.67-0.84 (m, 2H) 1.12-1.21 (m, 2H) 1.22-1.36 (m, 6H) 2.09-2.18 (m, 1H) 2.32 (s, 3H) 2.53 (d, J=3.20 Hz, 3H) 2.76-2.86 (m, 1H) 3.00 (d, J=5.09 Hz, 1H) 3.05-3.19 (m, 2H) 3.24-3.52 (m, 2H) 3.66 (br. s., 1H) 4.05 (q, J=7.03 Hz, 2H) 6.68 (br. s., 1H) 6.76 (br. s., 1H) 8.09 (s, 1H) 9.16 (br. s., 1H) 9.58 (br. s., 1H) 10.31 (br. s., 1H) 11.31 (br. s., 1H) 13.90 (br. s., 1H). MS (ES$^+$), (M+H)$^+$=466.29 for $C_{24}H_{32}FN_9$.

Example 4

(R)—N2-(4-cyclopropyl-5-fluoro-6-methylpyridin-2-yl)-N4-(1-methyl-1H-1,2,3-triazol-4-yl)-5-(3-methylpiperazin-1-yl)pyrimidine-2,4-diamine dihydrochloride

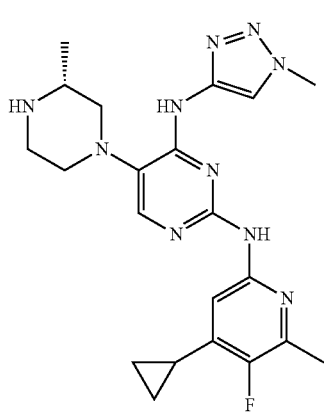 [SMILES: Cc1nc(Nc2ncc(N3CCN[C@H](C)C3)c(Nc3cn(C)nn3)n2)cc(C2CC2)c1F]

This was prepared as described above for Example 2 from Intermediate Xc. Yield: 92%, $^1$H NMR (300 MHz, DMSO-$d_6$) δ ppm 13.61-14.09 (m, 1H), 12.20 (br. s., 1H), 10.97 (s, 1H), 9.65 (br. s., 1H), 8.91-9.29 (m, 2H), 8.13 (s, 1H), 6.97 (d, J=4.90 Hz, 1H), 3.67 (br. s., 1H), 3.27-3.56 (m, 3H), 2.98-3.27 (m, 3H), 2.68-2.94 (m, 1H), 2.03-2.28 (m, 2H), 1.07-1.38 (m, 6H), 0.69-0.84 (m, 2H). MS (ES+), (M+H)+= 439.37 for $C_{21}H_{27}FN_{10}$.

Example 5

(R)—N2-(5-chloro-4-cyclopropyl-6-methylpyridin-2-yl)-N4-(1,5-dimethyl-1H-pyrazol-3-yl)-5-(3-methylpiperazin-1-yl)pyrimidine-2,4-diamine dihydrochloride

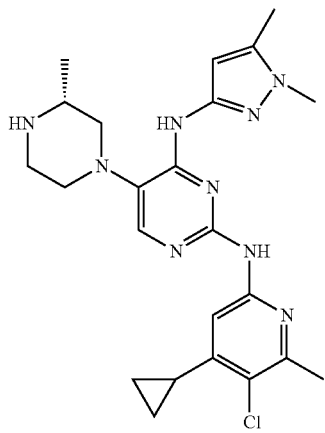 [SMILES: Cc1nc(Nc2ncc(N3CCN[C@H](C)C3)c(Nc3cc(C)n(C)n3)n2)cc(C2CC2)c1Cl]

This was prepared as described above for Example 2 from Intermediate Xd. Yield: 92%, $^1$H NMR (300 MHz, DMSO-$d_6$) δ 9.39 (s, 1H), 8.05 (s, 1H), 7.92-8.01 (m, 1H), 7.77 (s, 1H), 6.87 (s, 1H), 3.63 (s, 3H), 3.36-3.42 (m, 1H), 2.63-3.00 (m, 7H), 2.04-2.40 (m, 7H), 0.91-1.18 (m, 8H), 0.56-0.78 (m, 2H). MS (ES$^+$), (M+H)$^+$=468.40 for $C_{23}H_{30}ClN_9$.

Example 6

(R)-4-cyclopropyl-6-((4-((1,5-dimethyl-1H-pyrazol-3-yl)amino)-5-(3-methylpiperazin-1-yl)pyrimidin-2-yl)amino)-2-methylnicotinonitrile dihydrochloride

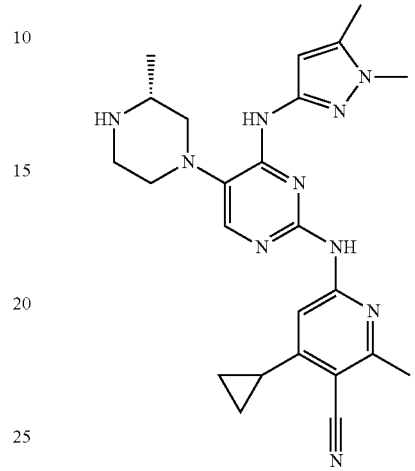

This was prepared as described above for Example 2 from Intermediate Xe. Yield: 91%, $^1$H NMR (300 MHz, DMSO-d6) δ ppm 1.19 (t, J=7.54 Hz, 3H) 1.28 (d, J=6.22 Hz, 3H) 2.31 (s, 3H) 2.54 (d, J=3.01 Hz, 3H) 2.68 (d, J=7.54 Hz, 2H) 2.77-2.87 (m, 1H) 3.12 (br. s., 2H) 3.27-3.39 (m, 1H) 3.44 (br. s., 1H) 3.64 (br. s., 1H) 3.73 (s, 3H) 6.72 (s, 1H) 7.17 (d, J=4.52 Hz, 1H) 8.12 (s, 1H) 9.28 (br. s., 1H) 9.71 (br. s., 1H) 10.27 (s, 1H) 11.48 (s, 1H) MS (ES$^+$), (M+H)$^+$=459.26 for $C_{24}H_{30}N_{10}$.

Example 7

(R)—N4-(1,5-dimethyl-1H-pyrazol-3-yl)-N2-(4-ethyl-5-fluoro-6-methylpyridin-2-yl)-5-(3-methylpiperazin-1-yl)pyrimidine-2,4-diamine dihydrochloride

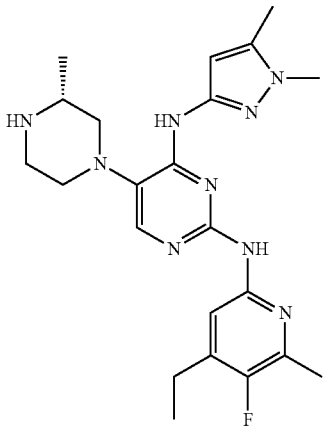 [SMILES: CCc1cc(Nc2ncc(N3CCN[C@H](C)C3)c(Nc3cc(C)n(C)n3)n2)nc(C)c1F]

This was prepared as described above for Example 2 from Intermediate Xf. Yield: 75%, $^1$H NMR (300 MHz, DMSO-$d_6$) δ ppm 1.15-1.24 (m, 3H) 1.29 (d, J=6.03 Hz, 3H) 2.31

(s, 3H) 2.54 (d, J=3.01 Hz, 3H) 2.67 (q, J=7.66 Hz, 2H) 2.85 (d, J=11.49 Hz, 1H) 2.96-3.22 (m, 3H) 3.24-3.54 (m, 4H) 3.60-3.76 (m, 4H) 6.74 (s, 1H) 7.18 (d, J=4.33 Hz, 1H) 8.13 (s, 1H) 9.40 (br. s., 1H) 9.82 (br. s., 1H) 10.28 (s, 1H) 11.52 (br. s., 1H) MS (ES$^+$), (M+H)$^+$=440.28 for $C_{22}H_{30}FN_9$.

Example 8

(R)—N4-(1,5-dimethyl-1H-pyrazol-3-yl)-N2-(4-ethyl-5-fluoro-6-methylpyridin-2-yl)-5-(3-methyl-piperazin-1-yl)pyrimidine-2,4-diamine dihydrochloride

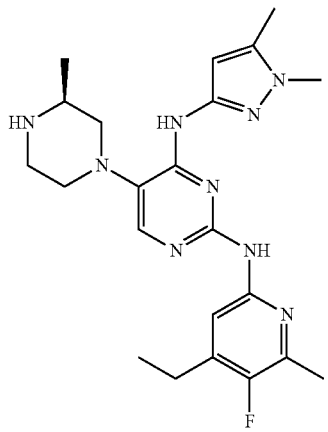 [SMILES: CCc1cc(Nc2ncc(N3CCN[C@@H](C)C3)c(Nc3cc(C)n(C)n3)n2)nc(C)c1F]

This was prepared as described above for Example 2 from Intermediate Xg. Yield: 75%, $^1$H NMR (300 MHz, DMSO-d$_6$) δ ppm 1.15-1.24 (m, 3H) 1.29 (d, J=6.03 Hz, 3H) 2.31 (s, 3H) 2.54 (d, J=3.01 Hz, 3H) 2.67 (q, J=7.66 Hz, 2H) 2.85 (d, J=11.49 Hz, 1H) 2.96-3.22 (m, 3H) 3.24-3.54 (m, 4H) 3.60-3.76 (m, 4H) 6.74 (s, 1H) 7.18 (d, J=4.33 Hz, 1H) 8.13 (s, 1H) 9.40 (br. s., 1H) 9.82 (br. s., 1H) 10.28 (s, 1H) 11.52 (br. s., 1H) MS (ES$^+$), (M+H)$^+$=440.28 for $C_{22}H_{30}FN_9$.

Example 9

(R)—N2-(4-cyclobutyl-5-fluoro-6-methylpyridin-2-yl)-N4-(1,5-dimethyl-1H-pyrazol-3-yl)-5-(3-methyl-piperazin-1-yl)pyrimidine-2,4-diamine dihydrochloride

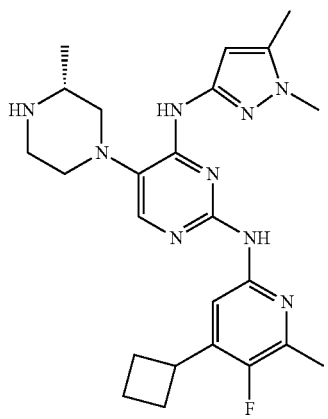 [SMILES: Cc1nc(Nc2ncc(N3CCN[C@H](C)C3)c(Nc3cc(C)n(C)n3)n2)cc(C2CCC2)c1F]

This was prepared as described above for Example 2 from Intermediate Xh. Yield: 99%, $^1$H NMR (300 MHz, DMSO-d$_6$) δ ppm 1.29 (d, J=6.40 Hz, 3H) 1.77-1.95 (m, 1H) 2.08-2.19 (m, 3H) 2.24-2.44 (m, 5H) 2.51-2.55 (m, 3H) 2.78-2.93 (m,1H) 2.98-3.19 (m, 3H) 3.31 (br. s., 1H) 3.40 (d, J=10.74 Hz, 1H) 3.57-3.80 (m, 5H) 6.78 (s, 1H) 7.22 (d, J=4.71 Hz, 1H) 8.14 (s, 1H) 9.47 (d, J=9.23 Hz, 1H) 9.92 (d, J=8.85 Hz, 1H) 10.31 (s, 1H) 11.57 (s, 1H) 13.96 (br. s., 1H). MS (ES$^+$), (M+H)$^+$=466 for $C_{24}H_{32}FN_9$.

Example 10

(R)—N2-(5-chloro-4-cyclopropyl-6-methylpyridin-2-yl)-N4-(2-methyl-2H-1,2,3-triazol-4-yl)-5-(3-methylpiperazin-1-yl)pyrimidine-2,4-diamine dihydochloride

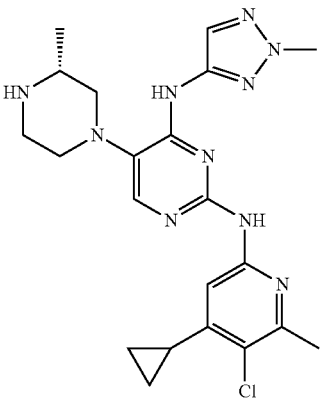 [SMILES: Cc1nc(Nc2ncc(N3CCN[C@H](C)C3)c(Nc3cnn(C)n3)n2)cc(C2CC2)c1Cl]

This was prepared as described above for Example 2 from Intermediate Xi. Yield: 99%, $^1$H NMR (300 MHz, DMSO-d$_6$) δ 0.63-0.88 (m, 2H) 1.14-1.37 (m, 6H), 2.19-2.34 (m, 1H), 2.68 (s, 4H), 2.83 (t, J=11.30 Hz, 1H), 2.95-3.25 (m, 4H), 3.29-3.59 (m, 3H), 4.17 (s, 4H), 6.82 (s, 1H), 8.21 (s, 1H), 8.46-8.63 (m, 1H), 9.33 (br. s., 1H), 9.81 (br. s., 1H), 10.90 (br. s., 1H), 11.73 (br. s., 1H), MS (ES$^+$), (M+H)$^+$=455 for $C_{21}H_{27}ClN_{10}$.

Example 11

(R)—N2-(5-chloro-4-cyclopropyl-6-methylpyridin-2-yl)-N4-(1-methyl-1H-1,2,3-triazol-4-yl)-5-(3-methylpiperazin-1-yl)pyrimidine-2,4-diamine dihydrochloride

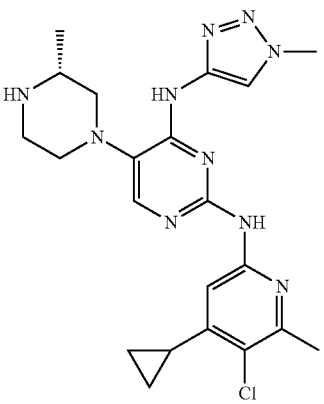 [SMILES: Cc1nc(Nc2ncc(N3CCN[C@H](C)C3)c(Nc3cn(C)nn3)n2)cc(C2CC2)c1Cl]

This was prepared as described above for Example 2 from Intermediate Xj. Yield: 79%, ¹H NMR (300 MHz, DMSO-d$_6$) δ 12.25 (br. s., 1H), 10.98 (br. s., 1H), 9.62 (br. s., 1H), 9.14 (br. s., 2H), 8.16 (s, 1H), 7.02 (br. s., 1H), 4.13 (s, 4H), 3.38 (s, 5H), 2.97-3.29 (m, 4H), 2.61-2.93 (m, 6H), 2.27 (br. s., 2H), 1.06-1.40 (m, 7H), 0.77 (br. s., 3H) MS (ES⁺), (M+H)⁺=455 for $C_{21}H_{27}ClN_{10}$.

Example 12

(R)—N2-(5-Fluoro-4-cyclopropyl-6-methylpyridin-2-yl)-N4-(2-methyl-2H-1,2,3-triazol-4-yl)-5-(3-methylpiperazin-1-yl)pyrimidine-2,4-diamine dihydochloride

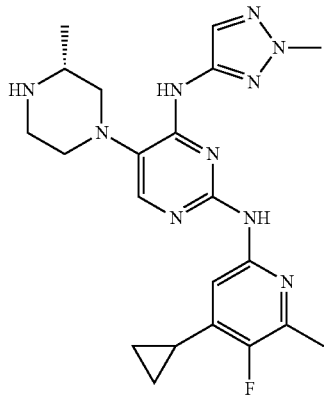 [SMILES: Cc1nc(Nc2ncc(N3CCN[C@H](C)C3)c(Nc3cnn(C)n3)n2)cc(C2CC2)c1F]

This was prepared as described above for Example 2 from Intermediate Xk. Yield: 92% MS (ES⁺), (M+H)⁺=438.36 for $C_{22}H_{28}FN_9$.

Example 13

(R)—N2-(4-cyclopropyl-5-fluoro-6-methylpyridin-2-yl)-N4-(1,5-dimethyl-1H-pyrazol-3-yl)-5-(3,4-dimethylpiperazin-1-yl)pyrimidine-2,4-diamine

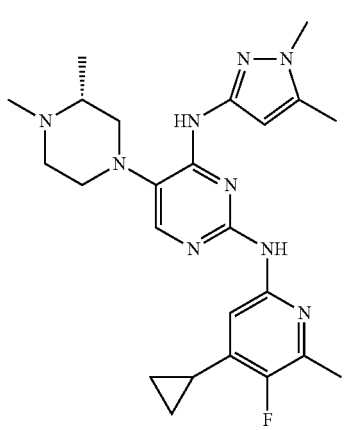

In a 50 mL round-bottom flask (R)—N2-(4-cyclopropyl-5-fluoro-6-methylpyridin-2-yl)-N4-(1,5-dimethyl-1H-pyrazol-3-yl)-5-(3-methylpiperazin-1-yl)pyrimidine-2,4-diamine hydrochloride (190 mg, 0.42 mmol, Example 2) was taken in DCM (2 mL) to give a yellow suspension. To this Hunig's Base (0.184 mL, 1.05 mmol) was added and the suspension turned clear. After 10 minutes, it turned into a white suspension. After another 10 minutes, the mixture was concentrated to dryness. Resultant residue was dissolved in ethanol (absolute, 99.5%) (3 mL) and formaldehyde (0.042 mL, 0.63 mmol) was added and stirred for 10 minutes. White suspension slowly cleared to yellow solution. To this clear solution sodium cyanoborohydride (26.4 mg, 0.42 mmol) was added in one portion to get white suspension. After 30 minutes LCMS showed completion of reaction. The reaction mixture was concentrated and the crude was purified through reverse phase HPLC GILSON instrument to get the pure solid of (R)—N2-(4-cyclopropyl-5-fluoro-6-methyl-pyridin-2-yl)-N4-(1,5-dimethyl-1H-pyrazol-3-yl)-5-(3,4-dimethylpiperazin-1-yl)pyrimidine-2,4-diamine (80 mg, 40.8%). ¹H NMR (300 MHz, DMSO-d$_6$) δ ppm 0.67-0.78 (m, 2H) 1.00 (d, J=6.22 Hz, 3H) 1.02-1.08 (m, 2H) 1.96-2.10 (m, 1H) 2.23 (s, 7H) 2.30-2.38 (m, 4H) 2.73-2.96 (m, 4H) 3.33 (s, 3H) 6.83 (s, 1H) 7.67 (d, J=5.09 Hz, 1H) 8.00 (s, 1H) 8.03 (s, 1H) 9.26 (s, 1H) MS (ES⁺), (M+H)⁺=466.45 for $C_{21}H_{32}FN_9$.

Example 14

(R)—N2-(4-cyclopropyl-5-fluoro-6-methylpyridin-2-yl)-5-(3,4-dimethylpiperazin-1-yl)-N4-(1-methyl-1H-1,2,3-triazol-4-yl)pyrimidine-2,4-diamine

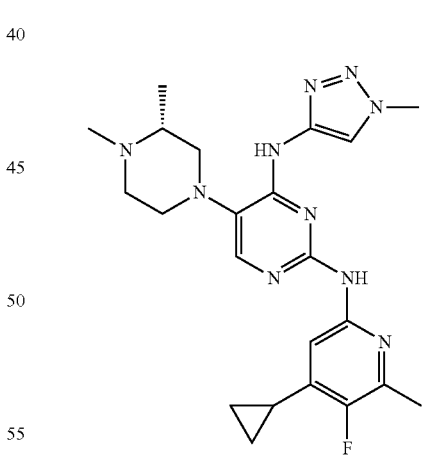

This was prepared as described above for Example 13 from Example 4. Yield: 12%, ¹H NMR (300 MHz, DMSO-d$_6$) δ ppm 0.71-0.81 (m, 2H) 0.81-0.90 (m, 1H) 1.01 (d, J=6.03 Hz, 3H) 1.05-1.16 (m, 2H) 1.20-1.32 (m, 2H) 1.99-2.13 (m, 1H) 2.24 (s, 3H) 2.36 (d, J=3.01 Hz, 4H) 2.69-2.98 (m, 5H) 2.69-2.98 (m, 5H) 4.05 (s, 3H) 7.76-7.94 (m, 1H) 8.05 (s, 1H) 8.40-8.60 (m, 1H) 8.92 (s, 1H) 9.47-9.71 (m, 1H). MS (ES⁺), (M+H)⁺=453.25 for $C_{22}H_{29}FN_{10}$.

Example 15

(R)—N2-(4-cyclopropyl-5-fluoro-6-methylpyridin-2-yl)-5-(3,4-dimethylpiperazin-1-yl)-N4-(2-methyl-2H-1,2,3-triazol-4-yl)pyrimidine-2,4-diamine

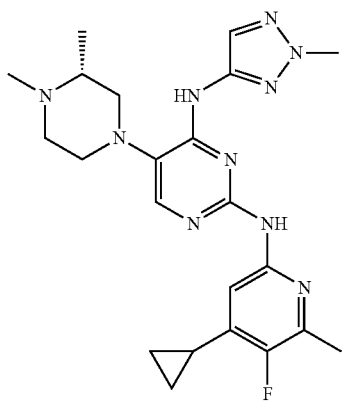

This was prepared as described above for Example 13 from Example 11. Yield: 28%, $^1$H NMR (300 MHz, DMSO-d6) δ ppm 2.28 (s, 3H) 3.78-4.09 (m, 5H) 5.76 (s, 2H) 5.97-6.51 (m, 1H) 7.36 (t, J=7.82 Hz, 1H) 7.71 (d, J=7.91 Hz, 1H) 7.91 (d, J=7.54 Hz, 1H) 8.41 (s, 1H) 8.57 (s, 1H) 10.05 (t, J=6.12 Hz, 1H). MS (ES$^+$), (M+H)$^+$=453.34 for $C_{22}H_{29}FN_{10}$.

Example 16

Biological Activities

The compounds of Formula (I) are of interest due to their potent antimalarial effects. The ability of the invention compounds disclosed herein to achieve an antimalarial effect may be evaluated with regard to their ability to inhibit the growth of Plasmodium species like P. falciparum using an assay based on the following protocol.

Further, compounds of the invention (Examples 2 and 13) were also tested against field isolates of falciparum and vivax malaria, along with three control antimalarials as described in the protocol below. The activity data are shown in Table 1.

TABLE 1

| Compounds | Plasmodium field isolates | |
|---|---|---|
| | P. falciparum IC$_{50}$ nM | P. vivax IC$_{50}$ nM |
| Chloroquine | 60.8 | 40.2 |
| Piperaquine | 16.9 | 5.9 |
| Artesunate | 15.1 | 4.79 |
| Example 13 | 74.6 | 85.6 |
| Example 2 | 63.6 | 81.0 |

These data support the fact that compounds of the invention have comparable activities towards falciparum and vivax malaria.

Measuring In Vitro Antiplasmodial Activity

The test samples were tested in duplicate on two separate occasions against chloroquine sensitive NF54 (MRA-1000, MR4, ATCC, Manassas, Va.) and chloroquine-resistant K1 strains of P. falciparum. A modified method of Trager and Jensen was employed to maintain continuous in vitro cultures of asexual blood stages of P. falciparum (Trager et al., 1976, Science, 193, 673-675). Quantitative assessment of antiplasmodial activity in vitro was determined using the SYBR I method as described earlier (Johnson et al., 2007, Antimicrob. Agents Chemother., 51, 1926-1933).

The percent inhibition with respect to the drug-free control was plotted against the logarithm of drug concentration. The growth inhibition curves were fitted by nonlinear regression using the sigmoidal dose-response (variable slope) formula to yield the concentration-response curves. The EC$_{50}$ value of the compound was defined as the lowest concentration at which 50% inhibition was observed. Chloroquine diphosphate (CQ) (Sigma), artesunate (Sigma), and pyrimethamine were used as reference drugs in all experiments.

The compounds of Formula (I) according to the invention were evaluated in an antimalarial activity test to determine their inhibitory activity against Plasmodium falciparum (both NF54 and K1 strains) and the results are reported in Table 2 below.

TABLE 2

| Example | Pf IC$_{50}$_NF54(nM) | Pf IC$_{50}$_K1(nM) |
|---|---|---|
| 1 | 15 | 24 |
| 2 | 14 | 19 |
| 3 | 17 | 14 |
| 4 | 33 | 51 |
| 5 | 23 | 48 |
| 6 | 31 | 45 |
| 7 | 27 | 45 |
| 8 | 35 | 44 |
| 9 | 25 | 48 |
| 10 | 13 | 19 |
| 11 | 30 | 50 |
| 12 | 39 | 82 |
| 13 | 9 | 15 |
| 14 | 33 | 69 |
| 15 | 17 | 37 |
| Chloroquinine | 11 | >150 |
| Pyrimethamine | 64 | 7900 |

In Vivo Efficacy in the Mouse Malaria Model

In vivo efficacy against blood stages was measured in mice infected with Plasmodium berghei after four (once daily) days of dosing by oral route. Detailed protocol for this four day suppressive test is described in Fidock et al 2004, Nature Reviews Drug Discovery (3), p 509. Percent inhibition of growth of parasites in mouse blood is shown in Table 3 below.

TABLE 3

| Compound | Dose (mg/kg) | % Inhibition |
|---|---|---|
| Example 7 | 3 | 6 |
| | 10 | 28 |
| | 30 | 100 |
| Example 10 | 10 | 60 |
| | 15 | 75 |
| | 30 | 100 |
| Example 13 | 3 | 0 |
| | 10 | 42 |
| | 30 | 100 |

Ex Vivo Activity of Examples 2 and 13 Against Drug Resistant P. falciparum and P. Vivax Field Isolates Standard antimalarial drugs chloroquine (CQ), amodiaquine (AQ), piperaquine (PIP), mefloquine (MFQ), and artesunate (AS) and compounds of the invention were prepared as 1 mg/mL stock solutions in H$_2$O or dimethyl sulfoxide (DMSO) according to the manufacturers' instructions. Drug plates were pre-dosed by diluting the compounds in 50% Methanol followed by lyophilisation and stored at 4° C.

*Plasmodium* isolates were collected from patients attending malaria clinics in Timika (Papua, Indonesia), a region endemic for multi-drug-resistant strains of *P. vivax* and *P. falciparum*. Patients with symptomatic malaria presenting to an outpatient facility were recruited into the study if singly infected with *P. falciparum* or *P. vivax*, with a parasitaemia of between 2,000 μl-1 and 80,000 μl-1, and the majority (>80%) of parasites at ring stage of development. Venous blood (5 mL) was collected by venipuncture and after removal of host white blood cells by using cellulose (Sigma-Aldrich, Australia) filtration, packed infected red blood cells (iRBCs) were used for the ex vivo drug susceptibility assay.

Drug susceptibility of *P. vivax* and *P. falciparum* isolates was measured using a protocol modified from the WHO microtest as described previously (Marfurt et al., 2011, *Antimicrob Agents Chemother.*, 55(9):4461). Two hundred μL of a 2% haematocrit Blood Media Mixture (BMM), consisting of RPMI 1640 medium plus 10% AB+ human serum (*P. falciparum*) or McCoy's 5 A medium plus 20% AB+ human serum (*P. vivax*), was added to each well of pre-dosed drug plates containing 11 serial concentrations (2-fold dilutions) of the antimalarials (maximum concentration shown in brackets) CQ (2,992 nM), AQ (158 nM), PIP (1,029 nM), MFQ (338 nM), AS (49 nM), and a compound of the invention (2,146 nM). A candle jar was used to mature the parasites at 37.0° C. for 35-56 hours. Incubation was stopped when >40% of ring stage parasites had reached mature schizont stage in the drug-free control wells.

Thick blood films made from each well were stained with 5% Giemsa solution for 30 minutes and examined microscopically. The number of schizonts per 200 asexual stage parasites was determined for each drug concentration and normalised to the control well. The dose-response data were analysed using nonlinear regression analysis (WinNonLn 4.1, Pharsight Corporation) and the IC$_{50}$ value derived using an inhibitory sigmoid Emax model. Ex vivo IC$_{50}$ data were only used from predicted curves where the E$_{max}$ and E$_0$ were within 15% of 100 and 1, respectively. Drug plate quality was assured by running schizont maturation assays (two independent experiments) with the chloroquine-resistant strain K1 and the chloroquine-sensitive strain FC27.

For microscopy slide reading QC, two randomly selected drugs per isolate were read by a second microscopist. If the raw data derived by the two microscopists led to a dramatic shift in the IC$_{50}$ estimates of the selected drugs, the whole assay (i.e., all standard drugs and experimental compounds) was re-read by a second reader and the results compared. If necessary, discrepant results were resolved by a third reading by an expert microscopist.

Metabolic Stability Assay (Rat/Human Hepatocyte Clint)

Viability of cryopreserved hepatocytes was determined using trypan blue and the cell concentration was adjusted to 10$^6$ cells per mL with Leibovitz L-15 Buffer. 1 μM compound (in Acetonitrile; 0.01% DMSO) was incubated with 500 μL of hepatocytes (1 million cells per mL) in a NUNC plate. Reaction was stopped at different time points (0, 5, 15, 30, 60, 90 and 120 min) by addition of 3 volumes of chilled acetonitrile to 100 μL of reaction mixture and centrifuged at 4° C. for 15 min. Supernatants were analyzed using LC-MS/MS for substrate depletion.

Determination of Blood:Plasma (BP) Ratio

The incubation plate and the dog blood/plasma was preheated at 37° C. for 10 minutes. 2 μL of working solution of each compound was added to 398 μL of dog reference plasma or blood to achieve a final concentration of 10 μM. Plates were incubated at 37° C. with shaking for 30 min. After incubation, the blood samples are spun for 10 min. at 4,000 rpm (37° C.) and the plasma samples were stored at 37° C. Aliquots (100 μL) of plasma separated from centrifuged whole blood samples and reference plasma samples were transferred into 96-well plates. 400 μL of cold acetonitrile was added to precipitate protein and release compound. After vortexing for 10 min., plates were centrifuged for 30 min. at 4,000 rpm. 250 μL of the supernatant was transferred to new 96-well plates and centrifuged again at 4,000 rpm for 30 min. 100 μL of the supernatant was used for analysis by LC-MS/MS.

Plasma Protein Binding Assay

Protein binding is measured using the equilibrium dialysis technique. Compound is added to 10% plasma giving a concentration of 20 μM and dialysed with isotonic buffer for 18 hours at 37° C. The plasma and buffer solutions are analysed using generic LCUVMS and the first apparent binding constant for the compound derived. The binding constant is then used to determine the % free in 100% plasma.

Prediction of Human Pharmacokinetic (PK) Parameters

Well stirred model was used for predicting human CL using human hepatocyte Clint and free fraction (fu) in human plasma. Liver blood flow rates, liver weights, hepatocellularity and in vitro in vivo correlation/extrapolation (IVIVC/E) templates routinely employed (Smith et al., *Pharmacokinetics and Metabolism in Drug Design, Methods and Principles in Medicinal Chemistry Volume* 13, 2004, Wiley-VCH, Weinheim, Germany) were used for prediction.

Pharmacokinetic Studies

All in vivo studies were approved by the institutional animal ethics committee. Pharmacokinetics following IV bolus (IVPK) or oral administration (POPK) of compounds was determined in male Wistar rats or male Beagle dogs. For IVPK in rats, Example 7 and Example 10 were administered as solutions in 20% DMA, 80% phosphate-buffered saline and Example 13 was administered as a solution in 10% v/v NMP, 20% v/v DMA in saline. For POPK, Example 7 and Example 10 were administered as suspensions in 20% DMA, 80% phosphate buffered saline and Example 13 administered as a suspension in 0.5% HPMC and 0.1% Tween 80 through an oral gavage. Example 13 was administered to dogs as a solution in 10% Ethanol, 30% PEG 400, 60% saline for IVPK and as a suspension in 0.5% HPMC, and 0.1% Tween 80 for POPK. Doses used for rat and dog PK were 0.5 mg/kg for Examples 7 and 10 or 2 mg/kg for Example 13 (IVPK). Doses of 5 mg/kg for Examples 7 and 10 were used during POPK. Doses of 10 mg/kg were used for Example 13 during POPK studies. Blood samples were collected at 8 to 13 time points (0, 0.0833, 0.25, 0.283, 0.333, 0.417, 0.75, 1.25, 3.25, 6.25, 12.25, 24.25 h for dog IVPK; 0, 0.25, 0.5, 1, 1.5, 2, 3, 4, 8, 12, 24, 32, 48 h for dog POPK; 0.083, 0.25, 0.5, 1, 2, 4, 7, 24 h for rat IVPK; 0.25, 1, 3, 6, 12, 24, 36, 48 h for rat POPK) after dosing. Blood (rat) or plasma (dog) samples were analysed by LC-MS/MS. PK parameters were estimated by non-compartmental analysis in Phoenix®.

Pharmacokinetics in the Blood of Infected Pf/SCID Mice:

Peripheral blood samples (25 μl) were taken at different times (0.25, 0.5, 1, 2, 4, 6, 8 and 23 hours), mixed with 25 l of H$_2$O mili Q and immediately frozen on dry ice. The frozen samples were stored at −80° C. until analysis.

Vehicle-treated mice experienced the same blood-sampling regimen. Blood samples were processed by liquid-liquid extraction by mixing 10 μl diluted blood with 180 μl AcN:MeOH (80:20; v:v) mixture. Quantitative analysis by LC/MSMS was performed using UPLC (Waters) and Sciex API4000. The lower limit of quantification (LLOQ) in this assay was 0.005 μg/ml.

CYP Inhibition Assay

This study was conducted using specific substrates for 5 major human CYP isozymes. These substrates were used as a cocktail (phenacetin, diclofenac, S-mephenytoin, bufuralol and midazolam which are predominantly metabolised by CYP 1A2, 2C9, 2C19, 2D6 and 3A4/5, respectively) at concentrations equivalent to their respective Km values. LC-MS-MS (MRM mode) was used to follow the formation of the CYP specific metabolites. A decrease in the formation of the metabolites in peak area to vehicle control was used to calculate the $IC_{50}$ value. In addition, as a positive control, a cocktail of five standard inhibitors, specific for an individual CYP (α-naphthoflavone, sulphaphenazole, N-3-benzylnirvanol, quinidine and ketoconazole, which specifically inhibit CYP 1A2, 2C9, 2C19, 2D6 and 3A4/5, respectively) was incubated. Test compound was used at 6 different concentrations (30, 10, 3, 1, 0.3, 0.1 M) to estimate $IC_{50}$.

The incubation was carried out in 96 deep well plates. Mixture of 180 μL of 20 mg/mL HLM and 90 μL of substrate cocktail solution was added to 15840 μL of phosphate buffer and 179 μL of this mixture was mixed with 1 μL of the test compound, inhibitor cocktail solution or vehicle in each well. The final concentration of DMSO:ACN in the assay mix was 0.3:0.7% v/v. The incubation plate was placed into the water bath and pre-warmed at 37° C. for 5 min before the reactions were started by the addition of 20 μL of 10 mmol/L NADPH solution in phosphate buffer. After the addition of NADPH, the incubation plate was incubated at 37° C. for a further 5 min. The reaction was quenched by the addition of 1 volume (200 μL) of cold ACN containing 3% formic acid and 40 nmol/L verapamil. The plates were kept on ice for 20 min and then centrifuged at 4000 rpm for 30 min to precipitate protein. The supernatant 180 μL was transferred to the analysis plate for LC/MS/MS analysis.

Caco-2 Permeability Assay

Permeability in a Caco-2 monolayer was determined at 10 μM. The Caco-2 cell monolayers were washed once with HBSS. TEER was measured both before and after performing all the transport experiments. Papp was measured in apical A to basolateral B direction. Transport buffer, 800 μL (HBSS, pH 7.4) was first dispensed to the basal side of the monolayer. The assay was then initiated by adding 200 μL of compound solution to the apical side (all test compounds were diluted in HBSS, pH 6.5, with 1% DMSO as co-solvent). Two μL and 200 μL of samples were withdrawn, before and at 45 and 120 min post addition of test compound, from the apical donor compartment and the basolateral receiver compartment, respectively. The transwell plates were incubated at 37° C. on a shaker at 480 rpm inside the incubator. All samples were immediately analysed by LC-MS/MS. A passive permeability was determined by complete chemical inhibition of the three major efflux transporters, ABCB1 (P-gp), ABCG2 (BCRP) and ABCC2 (MRP2), in Caco-2 cells using a cocktail of chemical inhibitors: quinidine (P-gp), sulfasalazine (BCRP) and benzbromarone (MRP2).

The apparent permeability coefficient ($P_{app}$) was calculated according to the following equation:

$$P_{app}=(\Delta Q/\Delta t)/(A \times C_D)[cm/s] \quad (1)$$

where $(\Delta Q/\Delta t)$ [cm/s] is the cumulative amount of test compound transported over time to the basolateral (receiver) side, A is the surface area of the monolayer membrane (cm$^2$) and $C_D$ is the average drug concentration in the donor chamber over the period for which $(\Delta Q/\Delta t)$ was determined. Hep Clint, PPB, BP ratio and predicted/observed pharmacokinetic properties are presented in Table 4 below.

TABLE 4

| Compound | Species | Hep. Clint (μl/min/1E6) | BP ratio | Fup | Predicted CLh blood (ml/min/kg) | CL blood (ml/min/kg) | Vss blood (L/kg) | Oral 'F' (%) | ½ life (PO PK) (h) |
|---|---|---|---|---|---|---|---|---|---|
| Ex. 10 | Rat | 8.3 | 1.7 | 0.04 | 16.10 | 22.5 | 9.7 | 17 | 30 |
| Ex. 13 | | 11.3 | 1.06 | 0.04 | 18.80 | 9.8 | 7.9 | 80 | 10 |
| Ex. 7 | | 5.6 | 2.2 | 0.06 | 24.20 | 26.6 | 12 | 31 | 10 |
| Ex. 10 | Dog | 5.1 | 1.7 | 0.04 | 12.70 | ND | ND | ND | ND |
| Ex. 13 | | 9.3 | 1.35 | 0.04 | 20.80 | 19.0 | 16.0 | 82 | 9 |
| Ex. 7 | | ND | ND | ND | ND | ND | ND | ND | ND |
| Ex. 10 | Human | 1.8 | 1.8 | 0.04 | 3.10 | ND | ND | ND | ND |
| Ex. 13 | | 3.1 | 1.1 | 0.03 | 4.80 | ND | ND | ND | ND |
| Ex. 7 | | 2.7 | 1.3 | 0.03 | 3.30 | ND | ND | ND | ND |

ND—not determined.

Since faster reduction in the blood parasite burden is essential to provide quick relief from clinical symptoms and to minimise the risk of emergence of drug resistance, the compounds of the invention were further evaluated for their in vitro PK/pharmacodynamic properties.

When tested in an in vitro parasite reduction ratio (PRR) assay (Le Manach, et al., 2013, *Malar J.*, 16, 424-430), Example 13 produced a >4-log kill after 48 hours of exposure, an effect similar to chloroquine in the same assay.

In the Pf/SCID model as described above, Example 13 cleared Pf parasites to below detection limit following 4 days of daily treatment with 20 mg/kg dose administered through the oral route. A maximum kill rate was observed at 40 mg/kg. Blood $C_{min}$ (0.04 μM) observed at this dose was considered the minimum parasiticidal concentration (MPC) for the human dose prediction.

CYP Inhibition

Examples 7, 10 and 13 did not inhibit human CYP 3A4, 2D6, 2C9, 2C19, or 1A2. The $IC_{50}s$ were >30 µM. The $IC_{50}s$ in the time dependent inhibition assays were >56 µM.

Caco-2 Permeability (pH 6.5/7.4)

Data are presented in Table 5 below.

TABLE 5

| Compound | Papp A to B (1E−6 cm/s) | Papp A to B (passive) (1E−6 cm/s) |
|---|---|---|
| Example 10 | 3.8 | 15.6 |
| Example 13 | 19.5 | 36.0 |
| Example 7 | 5.0 | 19.9 |

Identification of In Vivo Metabolites

Metabolites of Example 13 were identified both in vitro and in vivo using the following models:

In vitro: The compound of Example 13 was incubated with human (HLM) or rat (RLM) liver microsomes (1 mg/ml protein concentration in 100 mM phosphate buffer, pH 7.4) at a final concentration of 10 µM in the presence of 2 mM NADPH. The reactive intermediates were trapped by including 2 mM glutathione (GSH) or N-acetyl cysteine (NAC) in the reaction mix.

In vivo in bile duct cannulated rats: Example 13 was administered intravenously (IV) as a bolus through the jugular vein at a dose of 2 mg/kg or 4 mg/kg of body weight for control (n=3) or BDC rats (n=2), respectively. Blood samples were collected at 0.083, 0.25, 0.5, 1, 2, 4, 6, 8 and 24 h through the carotid artery, bile samples were collected at 0-2 h, 2-4 h, 4-6 h, 6-8 h and 8-24 h intervals and urine samples were collected at 0-8 h and 8-24 h intervals. The bile and urine samples were analyzed for the presence of parent and metabolites and blood samples were analyzed for the presence of parent. Data are presented in Table 6 below.

TABLE 6

| Presence of | Peak | Rt (min) | Proposed Metabolite (m/z) | Rat | Human | Mouse |
|---|---|---|---|---|---|---|
| Liver microsomes or Hepatocytes | Ex. 2 | 22.7 | N-demethylation (452) | ✓ | ✓ | ✓ |

These studies supported the fact that the compound of Example 2 is an active metabolite of the compound of Example 13 and is formed both in vitro and in vivo. Percent conversion to the active metabolite was highest in mouse, followed by rat and then human liver microsomes.

Importantly, there was no unique metabolite identified in the presence of HLM or Hu hepatocytes. There was no GSH or NAC adduct formation. Hence there were no reactive metabolites formed in vitro.

The invention claimed is:

1. A compound of Formula (I):

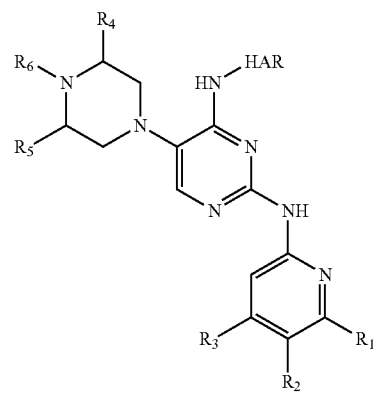

(I)

or a hydrate, solvate, or polymorph, tautomer, geometrical isomer, optically active form or a pharmaceutically acceptable salt thereof, wherein:

HAR is a 5 membered heteroaryl ring system selected from:

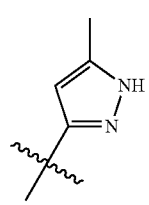

(a)

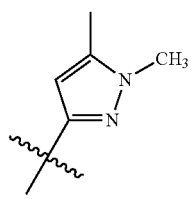

(b)

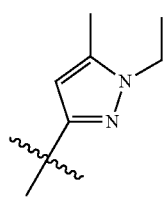

(c)

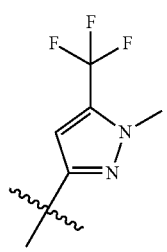

(d)

(e)

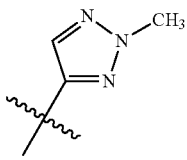

(f)

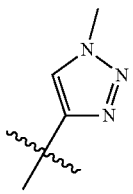

$R^1$ is independently selected from H, $C_{1-6}$ alkyl, $CF_3$ and $C_3$-$C_5$ cycloalkyl;
$R^2$ is independently selected from halo, —CN and $C_{1-6}$ alkyl;
$R^3$ is selected from H, $C_{1-6}$ alkyl, $C_3$-$C_5$ cycloalkyl and $CF_3$;
$R^4$ is independently selected from H and $C_{1-6}$ alkyl;
$R^5$ is independently selected from H and $C_{1-6}$ alkyl; and
$R^6$ is independently selected from H and $C_{1-6}$ alkyl.

2. The compound of claim 1, wherein $R^1$ is $C_{1-6}$ alkyl.
3. The compound of claim 1, wherein $R^2$ is halogen.
4. The compound of claim 1, wherein $R^3$ is $C_3$-$C_5$ cycloalkyl.
5. The compound of claim 1, wherein $R^3$ is $C_{1-6}$ alkyl.
6. The compound of claim 1, $R^4$ is $C_{1-6}$ alkyl.
7. The compound of claim 1, wherein $R^5$ is hydrogen.
8. The compound of claim 1, wherein $R^6$ is H.
9. The compound of claim 1, wherein $R^6$ is $C_{1-6}$ alkyl.
10. The compound of claim 1, wherein HAR is selected from the following group:

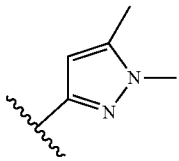 and 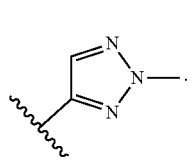

11. The compound of claim 1, wherein $R^1$ is methyl; $R^2$ is selected from fluorine, chlorine and CN; $R^3$ is selected from cyclobutyl, ethyl and cyclopropyl; $R^4$ is selected from hydrogen and methyl; $R^5$ is hydrogen; $R^6$ is selected from hydrogen and methyl; and HAR is selected from:

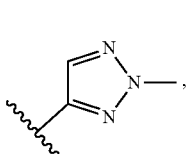 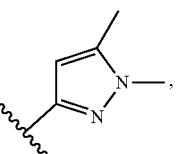

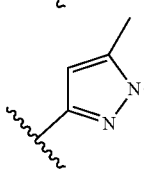 and 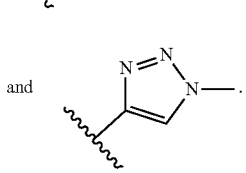

12. The compound of claim 1, wherein the compound is selected from the following group:
N2-(4-cyclopropyl-5-fluoro-6-methyl-2-pyridyl)-5-(4-methylpiperazin-1-yl)-N4-(1-methyltriazol-4-yl)pyrimidine-2,4-diamine;
N2-(4-cyclopropyl-5-fluoro-6-methyl-2-pyridyl)-N4-(1,5-dimethylpyrazol-3-yl)-5-[3-methylpiperazin-1-yl]pyrimidine-2,4-diamine;
N2-(4-cyclopropyl-5-fluoro-6-methyl-2-pyridyl)-N4-(1-ethyl-5-methyl-pyrazol-3-yl)-5-[3-methylpiperazin-1-yl]pyrimidine-2,4-diamine;
N2-(4-cyclopropyl-5-fluoro-6-methyl-2-pyridyl)-5-[(3R)-3-methylpiperazin-1-yl]-N4-(1-methyltriazol-4-yl)pyrimidine-2,4-diamine;
N2-(5-chloro-4-cyclopropyl-6-methyl-2-pyridyl)-N4-(1,5-dimethylpyrazol-3-yl)-5-[3-methylpiperazin-1-yl]pyrimidine-2,4-diamine;
4-cyclopropyl-6-[[4-[(1,5-dimethylpyrazol-3-yl)amino]-5-[3-methylpiperazin-1-yl]pyrimidin-2-yl]amino]-2-methyl-pyridine-3-carbonitrile;
N4-(1,5-dimethylpyrazol-3-yl)-N2-(4-ethyl-5-fluoro-6-methyl-2-pyridyl)-5-[3-methylpiperazin-1-yl]pyrimidine-2,4-diamine;
N4-(1,5-dimethylpyrazol-3-yl)-N2-(4-ethyl-5-fluoro-6-methyl-2-pyridyl)-5-[3-methylpiperazin-1-yl]pyrimidine-2,4-diamine;
N2-(4-cyclobutyl-5-fluoro-6-methyl-2-pyridyl)-N4-(1,5-dimethylpyrazol-3-yl)-5-[3-methylpiperazin-1-yl]pyrimidine-2,4-diamine;
N2-(5-chloro-4-cyclopropyl-6-methyl-2-pyridyl)-5-[3-methylpiperazin-1-yl]-N4-(2-methyltriazol-4-yl)pyrimidine-2,4-diamine;
N2-(5-chloro-4-cyclopropyl-6-methyl-2-pyridyl)-5-[3-methylpiperazin-1-yl]-N4-(1-methyltriazol-4-yl)pyrimidine-2,4-diamine;
N2-(5-chloro-4-cyclopropyl-6-methyl-2-pyridyl)-5-[3-methylpiperazin-1-yl]-N4-(2-methyltriazol-4-yl)pyrimidine-2,4-diamine;
N2-(4-cyclopropyl-5-fluoro-6-methyl-2-pyridyl)-5-[3,4-dimethylpiperazin-1-yl]-N4-(1,5-dimethylpyrazol-3-yl)pyrimidine-2,4-diamine;
N2-(4-cyclopropyl-5-fluoro-6-methyl-2-pyridyl)-5-[3,4-dimethylpiperazin-1-yl]-N4-(1-methyltriazol-4-yl)pyrimidine-2,4-diamine; and
N2-(4-cyclopropyl-5-fluoro-6-methyl-2-pyridyl)-5-[3,4-dimethylpiperazin-1-yl]-N4-(2-methyltriazol-4-yl)pyrimidine-2,4-diamine;
as well as pharmaceutically acceptable salts, complexes, hydrates, solvates, tautomers, polymorphs, racemic mixtures, optically active forms and pharmaceutically active derivative thereof.

13. The compound of claim 1, wherein the compound is selected from N2-(4-cyclopropyl-5-fluoro-6-methyl-2-pyridyl)-5-[3,4-dimethylpiperazin-1-yl]-N4-(1,5-dimethylpyrazol-3-yl)pyrimidine-2,4-diamine and its active metabolite N2-(4-cyclopropyl-5-fluoro-6-methyl-2-pyridyl)-N4-(1,5-dimethylpyrazol-3-yl)-5-[3-methylpiperazin-1-yl]pyrimidine-2,4-diamine.

14. The compound of claim 1, wherein the compound is N4-(1,5-dimethylpyrazol-3-yl)-N2-(4-ethyl-5-fluoro-6-methyl-2-pyridyl)-5-[3-methylpiperazin-1-yl]pyrimidine-2,4-diamine.

15. The compound of claim 1, wherein N2-(5-chloro-4-cyclopropyl-6-methyl-2-pyridyl)-5-[3-methylpiperazin-1-yl]-N4-(2-methyltriazol-4-yl)pyrimidine-2,4-diamine.

16. The compound of claim 1, wherein the compound is an R enantiomer.

17. A pharmaceutical composition comprising a compound of claim 1, or a pharmaceutically acceptable salt thereof, and a pharmaceutically acceptable diluent, excipient or carrier.

18. The pharmaceutical composition of claim 17 further comprising at least one further antimalarial agent.

19. The pharmaceutical composition of claim 18 wherein the further antimalarial agent is selected from artemisinin or an artimisinin derivative, chloroquinine, mefloquine, quinine, atoquone/proguanil, doxycycline, hydroxychloroquinine, halofantrine, pyronaridine, lumefantrine, pyrmethamine-sulfadoxine, piperaquine, amodiaquine, atovaquone, proguanil hydrochloride, Spiro[3H-indole-3,1'-[1H]pyrido[3,4-b]indol]-2(1H)-one-5,7'-dichloro-6'-fluoro-2',3',4',9'-tetrahydro-3'-methyl-,(1'R,3'S)-], Sulfur, [4-[[2-(1,1-difluoroethyl)-5-methyl[1,2,4]triazolo[1,5-a]pyrimidin-7-yl]amino]phenyl]pentafluoro-], Morpholine, 4-[2-(4-cis-dispiro[cyclohexane-1,3'-[1,2,4]trioxolane-5',2"-tricyclo[3.3.1.1³,⁷]decan]-4-yl phenoxy)ethyl]-], quinacrine, primaquine, tafenaquine, doxycycline, ferroquine, and arterolane.

20. A method of treating malaria or a parasitic infection caused by *plasmodium* species, comprising administering to a warm-blooded animal in need thereof an effective amount of a compound of claim 1 or hydrate, solvate, or polymorph, tautomer, geometrical isomer, optically active form or pharmaceutically acceptable salt thereof or a pharmaceutical composition thereof.

21. The method of claim 20, wherein the compound is administered in combination with a co-agent useful in the treatment of malaria.

22. A process for the preparation of a compound of Formula (I) comprising the step of reacting a derivative according to Formula (X) to form a compound of Formula (I) under acidic conditions:

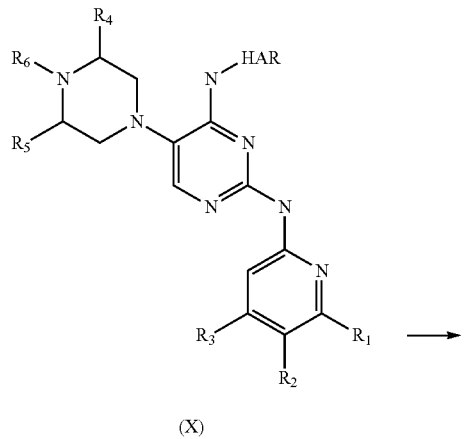

(X)

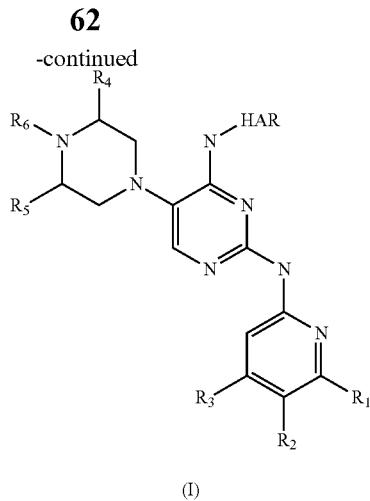

(I)

wherein $R_1$, $R_2$, $R_3$, $R_4$, $R_5$ and HAR are as defined in claim 1 and R is a protecting group.

23. A process for the preparation of an compound of Formula (I) comprising the step of reacting a derivative according to Formula (IV) with a derivative of Formula (V) to to form an intermediate compound of Formula (X) under palladium catalysed amination conditions as follows:

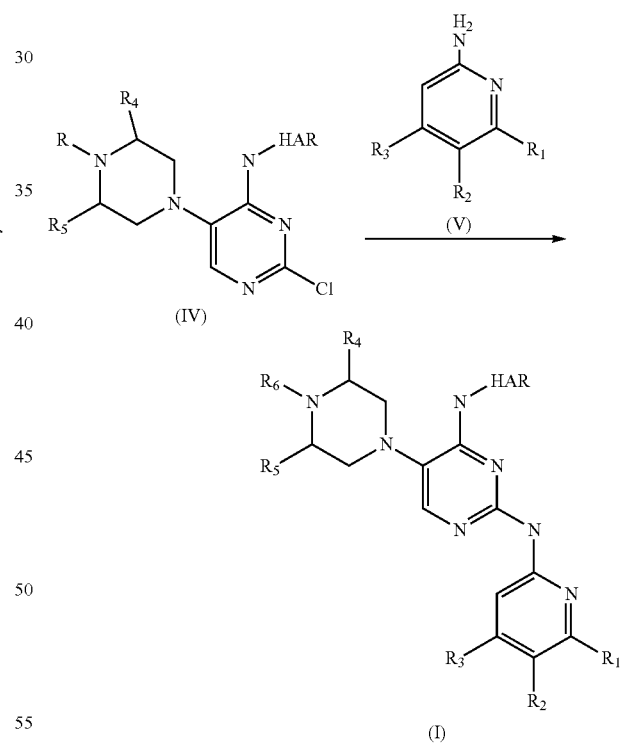

(I)

wherein R is $R^6$ and $R^6$ is alkyl.

* * * * *

UNITED STATES PATENT AND TRADEMARK OFFICE
CERTIFICATE OF CORRECTION

Page 1 of 1

PATENT NO. : 9,957,253 B2
APPLICATION NO. : 15/307382
DATED : May 1, 2018
INVENTOR(S) : Shahul Hameed Peer Mohamed et al.

It is certified that error appears in the above-identified patent and that said Letters Patent is hereby corrected as shown below:

In the Specification

Column 33,
Line 18, "Intermediate Via" should read --Intermediate VIa--.

In the Claims

Column 62,
Lines 24-25, "Formula (V) to to form" should read --Formula (V) to form--.

Signed and Sealed this
Twenty-third Day of July, 2019

Andrei Iancu
*Director of the United States Patent and Trademark Office*